United States Patent
Ullrich, Jr. et al.

(10) Patent No.: US 9,848,995 B2
(45) Date of Patent: Dec. 26, 2017

(54) PROCESS FOR FABRICATING BIOACTIVE VERTEBRAL ENDPLATE BONE-CONTACTING SURFACES ON A SPINAL IMPLANT

(71) Applicant: Titan Spine, LLC, Mequon, WI (US)

(72) Inventors: Peter F. Ullrich, Jr., Neenah, WI (US); Chad J. Patterson, Port Washington, WI (US); Jennifer M. Schneider, Germantown, WI (US); Mark E. Berg, Mequon, WI (US)

(73) Assignee: Titan Spine LLC, Mequon, WI (US)

( * ) Notice: Subject to any disclaimer, the term of this patent is extended or adjusted under 35 U.S.C. 154(b) by 0 days.

(21) Appl. No.: 14/486,285

(22) Filed: Sep. 15, 2014

(65) Prior Publication Data

US 2015/0018958 A1 Jan. 15, 2015

Related U.S. Application Data

(63) Continuation of application No. PCT/US2013/032943, filed on Mar. 19, 2013.
(Continued)

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/3094* (2013.01); *A61F 2/4455* (2013.01);
(Continued)

(58) Field of Classification Search
CPC ................ A61F 2/30767; A61F 2/3094; A61F 2002/30906; A61F 2002/30925;
(Continued)

(56) References Cited

U.S. PATENT DOCUMENTS

| 4,314,876 A | 2/1982 | Kremer et al. |
| 4,818,559 A * | 4/1989 | Hama ................. A61C 8/0012 424/423 |

(Continued)

FOREIGN PATENT DOCUMENTS

| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Ellen C Hammond
(74) *Attorney, Agent, or Firm* — Stradley Ronon Stevens & Young, LLP

(57) ABSTRACT

An interbody spinal implant including a body having a top surface, a bottom surface, opposing lateral sides, and opposing anterior and posterior portions. At least a portion of the top surface, the bottom surface, or both surfaces has a roughened surface topography including both micro features and nano features, without sharp teeth that risk damage to bone structures, adapted to grip bone through friction generated when the implant is placed between two vertebrae and to inhibit migration of the implant. The roughened surface topography typically further includes macro features and the macro features, micro features, and nano features overlap. Also disclosed are methods of using such implants and processes of fabricating a roughened surface topography on a surface of an implant. The process includes separate and sequential macro processing, micro processing, and nano processing steps.

20 Claims, 19 Drawing Sheets

Related U.S. Application Data

(60) Provisional application No. 61/613,108, filed on Mar. 20, 2012.

(51) Int. Cl.
*A61F 2/30* (2006.01)
*A61F 2/28* (2006.01)

(52) U.S. Cl.
CPC .......... *A61F 2/4465* (2013.01); *A61F 2/4611* (2013.01); *A61F 2/30965* (2013.01); *A61F 2002/2817* (2013.01); *A61F 2002/2835* (2013.01); *A61F 2002/30013* (2013.01); *A61F 2002/3084* (2013.01); *A61F 2002/3092* (2013.01); *A61F 2002/3093* (2013.01); *A61F 2002/3097* (2013.01); *A61F 2002/30321* (2013.01); *A61F 2002/30454* (2013.01); *A61F 2002/30772* (2013.01); *A61F 2002/30774* (2013.01); *A61F 2002/30779* (2013.01); *A61F 2002/30836* (2013.01); *A61F 2002/30838* (2013.01); *A61F 2002/30904* (2013.01); *A61F 2002/30906* (2013.01); *A61F 2002/30925* (2013.01); *A61F 2002/30927* (2013.01); *A61F 2002/4475* (2013.01); *A61F 2002/4629* (2013.01); *A61F 2310/00017* (2013.01); *A61F 2310/00023* (2013.01); *A61F 2310/00161* (2013.01); *A61F 2310/00179* (2013.01); *A61F 2310/00329* (2013.01); *Y10T 29/49995* (2015.01)

(58) Field of Classification Search
CPC .. A61F 2002/30929; A61F 2002/30838; A61F 2002/3084
See application file for complete search history.

(56) References Cited

U.S. PATENT DOCUMENTS

| | | |
|---|---|---|
| 4,834,757 A | 5/1989 | Brantigan |
| 4,904,261 A | 2/1990 | Dove et al. |
| 5,015,247 A | 5/1991 | Michelson |
| 5,071,437 A | 12/1991 | Steffee |
| 5,258,098 A * | 11/1993 | Wagner ............ A61F 2/30767 216/41 |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A * | 10/1995 | Steinemann ........ A61F 2/30767 606/76 |
| 5,507,815 A | 4/1996 | Wagner et al. |
| 5,571,188 A | 11/1996 | Ellingsen et al. |
| 5,603,338 A | 2/1997 | Beaty |
| 5,609,635 A | 3/1997 | Michelson |
| 5,702,449 A | 12/1997 | McKay |
| 5,755,798 A | 5/1998 | Papavero et al. |
| 5,766,252 A | 6/1998 | Henry et al. |
| 5,776,199 A | 7/1998 | Michelson |
| 5,860,973 A | 1/1999 | Michelson |
| 5,863,201 A | 1/1999 | Lazzara et al. |
| 5,865,845 A | 2/1999 | Thalgott |
| 5,876,453 A | 3/1999 | Beaty |
| 5,885,079 A | 3/1999 | Niznick |
| 5,888,224 A | 3/1999 | Beckers et al. |
| 5,922,029 A | 7/1999 | Wagner et al. |
| 5,968,098 A | 10/1999 | Winslow |
| 5,984,922 A | 11/1999 | McKay |
| 6,033,582 A | 3/2000 | Lee et al. |
| 6,039,762 A | 3/2000 | McKay |
| 6,059,829 A | 5/2000 | Schlaepfer et al. |
| 6,080,158 A | 6/2000 | Lin |
| 6,086,613 A | 7/2000 | Camino et al. |
| 6,096,107 A | 8/2000 | Caracostas et al. |
| 6,123,705 A | 9/2000 | Michelson |
| 6,143,032 A | 11/2000 | Schafer et al. |
| 6,176,882 B1 | 1/2001 | Biedermann et al. |
| 6,183,255 B1 | 2/2001 | Oshida |
| 6,193,757 B1 | 2/2001 | Foley et al. |
| 6,193,762 B1 | 2/2001 | Wagner et al. |
| 6,241,770 B1 | 6/2001 | Michelson |
| 6,241,771 B1 | 6/2001 | Gresser et al. |
| 6,245,108 B1 | 6/2001 | Biscup |
| 6,296,664 B1 | 10/2001 | Middleton |
| 6,302,914 B1 | 10/2001 | Michelson |
| 6,325,827 B1 | 12/2001 | Lin |
| 6,342,074 B1 | 1/2002 | Simpson |
| 6,344,057 B1 | 2/2002 | Rabbe et al. |
| 6,344,061 B1 * | 2/2002 | Leitao ............... A61F 2/30767 424/423 |
| 6,350,283 B1 | 2/2002 | Michelson |
| 6,375,681 B1 | 4/2002 | Truscott |
| 6,387,130 B1 | 5/2002 | Stone et al. |
| 6,395,031 B1 | 5/2002 | Foley et al. |
| 6,423,095 B1 | 7/2002 | Van Hoeck et al. |
| 6,425,920 B1 | 7/2002 | Hamada |
| 6,432,140 B1 | 8/2002 | Lin |
| 6,436,102 B1 | 8/2002 | Ralph et al. |
| 6,447,544 B1 | 9/2002 | Michelson |
| 6,458,159 B1 | 10/2002 | Thalgott |
| 6,478,823 B1 | 11/2002 | Michelson |
| 6,482,233 B1 | 11/2002 | Aebi et al. |
| 6,485,517 B1 | 11/2002 | Michelson |
| 6,491,723 B1 | 12/2002 | Beaty |
| 6,520,993 B2 | 2/2003 | James et al. |
| 6,558,424 B2 | 5/2003 | Thalgott |
| 6,569,201 B2 | 5/2003 | Moumene et al. |
| 6,579,318 B2 | 6/2003 | Varga et al. |
| 6,592,624 B1 | 7/2003 | Fraser et al. |
| 6,599,322 B1 | 7/2003 | Amrich et al. |
| 6,610,089 B1 | 8/2003 | Liu et al. |
| 6,620,332 B2 | 9/2003 | Amrich |
| 6,635,086 B2 | 10/2003 | Lin |
| 6,652,765 B1 | 11/2003 | Beaty |
| 6,676,703 B2 | 1/2004 | Biscup |
| 6,702,855 B1 | 3/2004 | Steinemann et al. |
| 6,719,794 B2 | 4/2004 | Gerber et al. |
| 6,726,720 B2 | 4/2004 | Ross et al. |
| 6,730,127 B2 | 5/2004 | Michelson |
| 6,740,118 B2 | 5/2004 | Eisermann et al. |
| 6,743,231 B1 | 6/2004 | Gray et al. |
| 6,758,849 B1 | 7/2004 | Michelson |
| 6,833,006 B2 | 12/2004 | Foley et al. |
| 6,890,355 B2 | 5/2005 | Michelson |
| 6,902,581 B2 | 6/2005 | Walkenhorst et al. |
| 6,911,249 B2 | 6/2005 | Wagner et al. |
| 6,923,810 B1 | 8/2005 | Michelson |
| 6,964,687 B1 | 11/2005 | Bernard et al. |
| 6,974,480 B2 | 12/2005 | Messerli et al. |
| 6,981,975 B2 | 1/2006 | Michelson |
| 7,018,412 B2 | 3/2006 | Ferreira et al. |
| 7,018,418 B2 | 3/2006 | Amrich et al. |
| 7,041,137 B2 | 5/2006 | Fulton et al. |
| 7,044,972 B2 | 5/2006 | Mathys, Jr. et al. |
| 7,048,870 B1 | 5/2006 | Ellingsen et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,085 B2 | 8/2006 | Steinemann et al. |
| 7,112,224 B2 | 9/2006 | Liu et al. |
| 7,128,760 B2 | 10/2006 | Michelson |
| 7,137,997 B2 | 11/2006 | Paul |
| 7,141,068 B2 | 11/2006 | Ross et al. |
| 7,144,428 B2 | 12/2006 | Anitua |
| 7,166,129 B2 | 1/2007 | Michelson |
| 7,169,183 B2 | 1/2007 | Liu et al. |
| D539,934 S | 4/2007 | Blain |
| 7,201,775 B2 | 4/2007 | Gorensek et al. |
| D541,940 S | 5/2007 | Blain |
| 7,220,280 B2 | 5/2007 | Kast et al. |
| 7,223,289 B2 | 5/2007 | Trieu et al. |
| 7,226,480 B2 | 6/2007 | Thalgott |

(56) References Cited

U.S. PATENT DOCUMENTS

| | | |
|---|---|---|
| 7,238,186 B2 | 7/2007 | Zdeblick et al. |
| 7,244,275 B2 | 7/2007 | Michelson |
| 7,250,060 B2 | 7/2007 | Trieu |
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |
| 7,368,065 B2 * | 5/2008 | Yang .................... A61L 27/047 216/103 |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,157,864 B2 | 4/2012 | Rogeau et al. |
| 8,172,854 B2 | 5/2012 | Blain et al. |
| 8,262,737 B2 * | 9/2012 | Bagga .................... A61F 2/442 623/17.11 |
| 8,323,348 B2 * | 12/2012 | Lai ........................ A61L 27/06 623/23.5 |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0156529 A1 | 10/2002 | Li et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0083668 A1 | 5/2003 | Rogers et al. |
| 2003/0105527 A1 | 6/2003 | Bresina |
| 2003/0109928 A1 | 6/2003 | Pasquet et al. |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0073314 A1 | 4/2004 | White et al. |
| 2004/0117019 A1 | 6/2004 | Trieu et al. |
| 2004/0117020 A1 | 6/2004 | Frey et al. |
| 2004/0122518 A1 | 6/2004 | Rhoda |
| 2004/0127993 A1 | 7/2004 | Kast et al. |
| 2004/0134886 A1 | 7/2004 | Wagner et al. |
| 2004/0153154 A1 * | 8/2004 | Dinkelacker ........ A61C 8/0012 623/16.11 |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 * | 10/2004 | Denzer ................ A61C 8/0012 623/16.11 |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0112397 A1 | 5/2005 | Rolfe |
| 2005/0119758 A1 | 6/2005 | Alexander et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1 | 9/2005 | Pope et al. |
| 2005/0251257 A1 | 11/2005 | Mitchell et al. |
| 2006/0025860 A1 | 2/2006 | Li |
| 2006/0030943 A1 | 2/2006 | Peterman |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0173938 A1 | 7/2007 | Sweeney |
| 2007/0203584 A1 | 8/2007 | Bandyopadhyay |
| 2007/0208343 A1 | 9/2007 | Magerl et al. |
| 2007/0213826 A1 | 9/2007 | Smith et al. |
| 2007/0213832 A1 | 9/2007 | Wen |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270839 A1 | 11/2007 | Jeon et al. |
| 2007/0270951 A1 | 11/2007 | Davis et al. |
| 2007/0270956 A1 | 11/2007 | Heinz |
| 2007/0276492 A1 | 11/2007 | Andrews |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0109081 A1 | 5/2008 | Bao et al. |
| 2008/0154378 A1 | 6/2008 | Pelo |
| 2008/0195209 A1 | 8/2008 | Garcia et al. |
| 2008/0213726 A1 * | 9/2008 | Schlottig ................ A61L 27/56 433/201.1 |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1 | 1/2009 | White et al. |
| 2009/0014243 A1 | 1/2009 | Whingham |
| 2009/0024132 A1 | 1/2009 | Blain et al. |
| 2009/0076614 A1 * | 3/2009 | Arramon ................ A61F 2/4425 623/17.16 |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182377 A1 | 7/2009 | Petersen |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |

(56) References Cited

U.S. PATENT DOCUMENTS

| | | |
|---|---|---|
| 2009/0264928 A1 | 10/2009 | Blain |
| 2009/0276049 A1 | 11/2009 | Weiland |
| 2009/0312837 A1 | 12/2009 | Eisermann et al. |
| 2010/0076559 A1 | 3/2010 | Bagga et al. |
| 2010/0094426 A1 | 4/2010 | Grohowski, Jr. et al. |
| 2010/0121385 A1 | 5/2010 | Blain et al. |
| 2010/0168798 A1 | 7/2010 | Clineff et al. |
| 2010/0173264 A1 | 7/2010 | Fredriksson et al. |
| 2010/0174382 A1* | 7/2010 | Gretzer .............. A61L 27/306 623/23.53 |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0268227 A1* | 10/2010 | Tong .................. A61L 27/46 606/60 |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1 | 1/2011 | Ankem |
| 2011/0033661 A1* | 2/2011 | Oawa .................. A61F 2/30 428/141 |
| 2011/0040301 A1 | 2/2011 | Blain et al. |
| 2011/0082503 A1 | 4/2011 | Blain |
| 2011/0151026 A1* | 6/2011 | Hansson ............. A61C 8/0012 424/722 |
| 2011/0190888 A1 | 8/2011 | Bertele et al. |
| 2011/0190902 A1* | 8/2011 | Tong .................. A61F 2/30767 623/23.5 |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1* | 11/2011 | Ullrich, Jr. ............ A61F 2/4465 623/17.16 |
| 2011/0318835 A1* | 12/2011 | Chen .................. A61L 27/06 435/375 |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0143341 A1* | 6/2012 | Zipnick ......... A61B 17/320016 623/17.16 |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ullrich, Jr. et al. |
| 2012/0239150 A1 | 9/2012 | Ullrich, Jr. et al. |
| 2012/0239151 A1 | 9/2012 | Ullrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |
| 2013/0013081 A1* | 1/2013 | Fredriksson ......... A61C 8/0012 623/23.5 |

FOREIGN PATENT DOCUMENTS

| | | |
|---|---|---|
| EP | 1440669 | 7/2004 |
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006119088 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2010010536 | 1/2010 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growith of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report dated Sep. 27, 2011.

Supplementary Partial European Search Report dated Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

Wennerberg, A., et al., "Effects of titanium surface topography on bone integration: a systematic review", Clin. Oral Impl. Res., 20 (Suppl. 4), 2009, pp. 172-184.

Pending U.S. Appl. No. 13/286,813 of Chad J. Patterson, et al. filed Nov. 1, 2011.

Pending U.S. Appl. No. 13/826,304 of Peter F. Ullrich, Jr., et al. filed Mar. 14, 2013.

Pending U.S. Appl. No. 13/713,417 of Chad J. Patterson, et al. filed Dec. 13, 2012.

International Search Report and Written Opinion issued in related application PCT/US2013/032943.

International Search Report and Written Opinion issued in related application PCT/US2013/050818.

European Search Report issued in related application EP 12 84 63676.

* cited by examiner

Ra = Average(1, 4, 6, 8, 5, 2, 1, 4, 1, 2, 1, 4, 7, 4, 1, 2, 5, 8, 2, 1, 4, 1, 1)

Ra = 3.26

Rpm = average(Rp1, Rp2, Rp3, ...)
Rvm = average(Rv1, Rv2, Rv3, ...)
RzDIN = Rtm = average(Rt1, Rt2, Rt3, ...)

Sm = average($S_1, S_2, S_3, ...$)

_US 9,848,995 B2_

PROCESS FOR FABRICATING BIOACTIVE VERTEBRAL ENDPLATE BONE-CONTACTING SURFACES ON A SPINAL IMPLANT

RELATED APPLICATION

This application is a continuation of International Application No. PCT/US2013/032943 filed Mar. 19, 2013, which claims the benefit of priority to U.S. Patent Application No. 61/613,108 filed on Mar. 20, 2012, the contents of which are incorporated in this application by reference.

TECHNICAL FIELD

The present invention relates generally to interbody spinal implants and methods of using such implants and, more particularly, to a friction-fit spinal implant having a roughened surface with features of predetermined sizes and shapes to achieve design trade offs depending upon a particular application.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Current techniques for implantation of orthopedic implants, including devices intended to replace soft tissue structures between two bones forming a joint, prescribe that the soft tissues and hard tissues are removed along with any damaged or diseased bone structures in order to expose sufficient vascularized or disease-free hard tissues for anchoring the implant in position. It has been taught that the exposure of bleeding vascularized soft bone delivers superior healing as the flow of blood and other biologic materials naturally occurring after injury is required. As with all other bones in the human body, the vertebrae are typically a hard, dense outer shell composed of dense cortical bone covering a low-density bone often referred to as cancellous or trabecular bone. In the case of spinal vertebrae, construction is composed of a very thin cortical bone forming a sealed cylindrical shape with higher densities at the connection between the cylindrical walls and the top and bottom surfaces which are referred to as endplates. This anatomic structure is named the apophyseal rim.

During a surgical procedure in the spine if this sealed vessel has been perforated it is believed that the semi-rigid structure opposing biologic loading is compromised and cannot heal and return to the proper function which it performs. It is also believed that if the high-density bone is removed exposing low-density cancellous bone and the implanted device does not have a stress-sharing surface of sufficient size to transfer loading it will allow the cancellous bone to be abraded further compromising the return to correct position. This condition is commonly referred to as degenerative disc disease. The consequent symptoms of pain and degraded function are among the reasons for typical interbody fusion procedures.

It is also believed the diagnosed condition of degenerative disc disease is where the position of the discs is moving together and causing compression of nerves located with the spinal column. Damage to the endplate surfaces over the long term will continue the progression of the condition regardless of the implantation of an intervertebral fusion implant. These endplates come in contact with the soft tissues that comprise the intervertebral discs. These discs function in several roles specifically maintaining the connection between vertebral bodies as a joint allowing for the natural motion required of the vertebral column structure while providing a location preservation and protective structure for the primary spinal cord and the subsequent branches connecting to the various biological structures within the body. Proper function is interrupted in cases where degenerative or traumatic events damage the intervertebral disc and this can have cascade injurious effects to the function and performance of the body.

Although the vertebra is constructed of hard high-density and low-density bone materials, it is also important to note that the structure is not completely rigid. Various aspects of vertebra performance while under biological loading have been studied and have shown that these structures undergo various amounts of movement across the diameter of the endplate face which is commonly ovoid in shape at different levels in the spinal column. In the lumbar vertebra this endplate serves a critical function of the overall vertebral body structure, having the ability to compress as the intervertebral disc is loaded. Preservation of this complex structure is critical to the preservation of the overall spinal column structure and long-term function of the spine.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants which better utilize the structurally supportive bone of the apophyseal rim.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory. Each of these challenges is addressed in turn.

1. End-Plate Preparation

There are three traditional end-plate preparation methods. The first is aggressive end-plate removal with box-chisel types of tools to create a nice match of end-plate geometry with implant geometry. In the process of aggressive end-plate removal, however, the end-plates are typically destroyed. Such destruction means that the load-bearing implant is pressed against soft cancellous bone and the implant tends to subside.

The second traditional end-plate preparation method preserves the end-plates by just removing cartilage with curettes. The end-plates are concave; hence, if a flat implant is used, the implant is not very stable. Even if a convex implant is used, it is very difficult to match the implant geometry with the end-plate geometry, as the end-plate geometry varies from patient-to-patient and on the extent of disease.

The third traditional end-plate preparation method uses threaded fusion cages. The cages are implanted by reaming out corresponding threads in the end-plates. This method also violates the structure.

2. Implant Difficulty

Traditional anterior spinal fusion devices can also be difficult to implant. Some traditional implants have sharp teeth. FIGS. 1A, 1B, and 1C illustrate the sharp "toothed" design common to these traditional implants. These teeth can bind to the surrounding soft tissue during implantation, creating surgical challenges. Specifically, FIG. 1A is a perspective view of a traditional implant 200 having sharp teeth 202 on its top and bottom surfaces. FIG. 1B is a side view of the traditional implant 200. FIG. 1C is an expanded view of a portion of the traditional implant 200 taken along the detail 1C illustrated in FIG. 1B, highlighting the regular pattern of sharp teeth 202.

Typically, secondary instrumentation is used to keep the disc space distracted during implantation. The use of such instrumentation means that the exposure needs to be large enough to accommodate the instrumentation. If there is a restriction on the exposure size, then the maximum size of the implant available for use is correspondingly limited. The need for secondary instrumentation for distraction during implantation also adds an additional step or two in surgery. Still further, secondary instrumentation may sometimes over-distract the annulus, reducing the ability of the annulus to compress a relatively undersized implant. The compression provided by the annulus on the implant is important to maintain the initial stability of the implant.

For anterior spinal surgery, there are traditionally three trajectories of implants: anterior, antero-lateral, and lateral. Each approach has its advantages and drawbacks. Sometimes the choice of the approach is dictated by surgeon preference, and sometimes it is dictated by patient anatomy and biomechanics. A typical traditional implant has design features to accommodate only one or two of these approaches in a single implant, restricting intra-operative flexibility.

3. Materials of Construction

Other challenges raised by traditional devices find their source in the conventional materials of construction. Typical devices are made of PEEK or cadaver bone. Materials such as PEEK or cadaver bone do not have the structural strength to withstand impact loads required during implantation and may fracture during implantation.

PEEK is an abbreviation for polyetherether-ketone, a high-performance engineering thermoplastic with excellent chemical and fatigue resistance plus thermal stability. With a maximum continuous working temperature of 480° F., PEEK offers superior mechanical properties. Superior chemical resistance has allowed PEEK to work effectively as a metal replacement in harsh environments. PEEK grades offer chemical and water resistance similar to PPS (polyphenylene sulfide), but can operate at higher temperatures. PEEK materials are inert to all common solvents and resist a wide range of organic and inorganic liquids. Thus, for hostile environments, PEEK is a high-strength alternative to fluoropolymers.

The use of cadaver bone has several drawbacks. The shapes and sizes of the implants are restricted by the bone from which the implant is machined. Cadaver bone carries with it the risk of disease transmission and raises shelf-life and storage issues. In addition, there is a limited supply of donor bone and, even when available, cadaver bone inherently offers inconsistent properties due to its variability. Finally, as mentioned above, cadaver bone has insufficient mechanical strength for clinical application.

4. Implant Expulsion

Traditional implants can migrate and expel out of the disc space, following the path through which the implant was inserted. Typical implants are either "threaded" into place, or have "teeth" which are designed to prevent expulsion. Both options can create localized stress risers in the end-plates, increasing the chances of subsidence. The challenge of preventing implant expulsion is especially acute for PEEK implants, because the material texture of PEEK is very smooth and "slippery."

5. Implant Subsidence

Subsidence of the implant is a complex issue and has been attributed to many factors. Some of these factors include aggressive removal of the end-plate; an implant stiffness significantly greater than the vertebral bone; smaller sized implants which tend to seat in the center of the disc space, against the weakest region of the end-plates; and implants with sharp edges which can cause localized stress fractures in the end-plates at the point of contact. The most common solution to the problem of subsidence is to choose a less stiff implant material. This is why PEEK and cadaver bone have become the most common materials for spinal fusion implants. PEEK is softer than cortical bone, but harder than cancellous bone.

6. Insufficient Room for Bone Graft

Cadaver bone implants are restricted in their size by the bone from which they are machined. Their wall thickness also has to be great to create sufficient structural integrity for their desired clinical application. These design restrictions do not leave much room for filling the bone graft material into cortical bone implants. The exposure-driven limitations on implant size narrow the room left inside the implant geometry for bone grafting even for metal implants. Such room is further reduced in the case of PEEK implants because their wall thickness needs to be greater as compared to metal implants due to structural strength needs.

7. Stress Shielding

For fusion to occur, the bone graft packed inside the implant needs to be loaded mechanically. Typically, however, the stiffness of the implant material is much greater than the adjacent vertebral bone and takes up a majority of the mechanical loads, "shielding" the bone graft material from becoming mechanically loaded. The most common solution is to choose a less stiff implant material. Again, this is why PEEK and cadaver bone have become the most common materials for spinal fusion implants. As noted above, although harder than cancellous bone, PEEK is softer than cortical bone.

8. Lack of Implant Incorporation with Vertebral Bone

In most cases, the typical fusion implant is not able to incorporate with the vertebral bone, even years after implantation. Such inability persists despite the use of a variety of different materials to construct the implants. There is a perception that cadaver bone is resorbable and will be replaced by new bone once it resorbs. Hedrocel is a composite material composed of carbon and tantalum, an inert metal, that has been used as a material for spinal fusion implants. Hedrocel is designed to allow bone in-growth into the implant. In contrast, PEEK has been reported to become surrounded by fibrous tissue which precludes it from incorporating with surrounding bone. There have also been reports of the development of new bio-active materials which can incorporate into bone. The application of such bio-active materials has been limited, however, for several reasons, including biocompatibility, structural strength, and lack of regulatory approval.

9. Limitations on Radiographic Visualization

For implants made out of metal, the metal prevents adequate radiographic visualization of the bone graft. Hence it is difficult to assess fusion, if it is to take place. PEEK is radiolucent. Traditional implants made of PEEK need to have radiographic markers embedded into the implants so that implant position can be tracked on an X-ray. Cadaver bone has some radiopacity and does not interfere with radiographic assessment as much as metal implants.

10. Cost of Manufacture and Inventory

The requirements of spinal surgery dictate that manufacturers provide implants of various foot-prints, and several heights in each foot-print. This requirement means that the manufacturer needs to carry a significant amount of inventory of implants. Because there are so many different sizes of implants, there are setup costs involved in the manufacture of each different size. The result is increased implant costs, which the manufacturers pass along to the end users by charging high prices for spinal fusion implants.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration.

As recognized in U.S. Patent Application Publication No. 2008-0262623 A1, titled "Composite Interbody Spinal Implant Having Openings of Predetermined Size and Shape" (the contents of which are fully incorporated by reference in this document) and owned by the assignee of the subject application, a surface roughened topography may better promote osteointegration. A surface roughened topography may also better grip the vertebral endplate surfaces and inhibit implant migration upon placement and seating.

A roughened topography may be obtained through a variety of techniques including chemical etching, shot peening, plasma etching, laser etching, or abrasive blasting (such as sand or grit blasting). More specifically, a roughened topography may be obtained via the repetitive masking and chemical or electrochemical milling processes described in U.S. Pat. Nos. 5,258,098; 5,507,815; 5,922,029; and 6,193,762. Each of these patents is incorporated in this document by reference. When chemical etching is used, for example, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control over the strength of the etchant material, over the temperature at which the etching process takes place, and over the time allotted for the etching process allows the user to dictate the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants may be comprised of titanium, or a titanium alloy, having an average surface roughness of about 100 µm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

To overcome the shortcomings of existing interbody spinal implants and methods of using such implants, a new implant and method are provided. An object of the present invention is to provide an improved friction-fit spinal implant having a roughened surface with features of predetermined sizes and shapes to achieve design trade-offs depending upon a particular application. Another object is to provide an implant having a surface with features in repeating patterns that can be used to resist biologic-induced motion after placement in a joint space in contact with bone structures.

It is still another object of the present invention to generate the surface features through a subtractive process that removes sharp edges that could abrade the ambient bone while still providing sufficient friction to resist expulsion or movement. A related object is to align these features to allow for insertion in opposition to a surface and to resist reverse motion from frictional contact with this surface. Another object of this invention is to use repeating patterns, depth of features, spacing of various shaped features and arraignment and overlapping of them in respect to others of a similar size and shape to develop designed composite patterns. Yet another object of the present invention is, as healing advances, to allow the surface modifications to work in concert with the ambient biological actions occurring during the healing and fusion process. A related object is to stimulate biological structures to produce biologic products that cause hard tissue formation with connections to the implant structure.

BRIEF SUMMARY OF THE INVENTION

To achieve these and other objects, and in view of its purposes, the present invention provides interbody spinal implants and methods of using such implants. The implants can be inserted, using methods of the present invention, from a variety of vantages, including anterior, antero-lateral, and lateral implantation. Certain embodiments of the present invention provide an anatomically shaped spinal implant for improved seating in the disc space, particularly in the medial-lateral aspect of the disc space, and improved utilization of the vertebral apophyseal rim. Certain embodiments of the present invention further have a highly radiused posterior portion and sides which allow for ease of implantation. Thus, the posterior portion may have a generally blunt nosed profile. Certain embodiments also allow for improved visualization of the disc space during surgical procedures while minimizing exposure of the operating space. Certain aspects of the invention reduce the need for additional instrumentation—such as chisels, reamers, or other tools—to prepare the vertebral endplate, thus minimizing the instrument load upon the surgeon.

Certain embodiments of the interbody implant are substantially hollow and have a generally oval-shaped transverse cross-sectional area. Substantially hollow, as used in this document, means at least about 33% of the interior volume of the interbody spinal implant is vacant. Further embodiments of the present invention include a body having a top surface, a bottom surface, opposing lateral sides, and opposing anterior and posterior portions. The implant includes at least one aperture that extends the entire height of the body. Thus, the aperture extends from the top surface to the bottom surface. The implant may further include at least one aperture that extends the entire transverse length of the implant body.

Still further, the substantially hollow portion may be filled with cancellous autograft bone, allograft bone, demineralized bone matrix (DBM), porous synthetic bone graft substitute, bone morphogenic protein (BMP), or combinations of those materials. The implant further includes a roughened surface topography on at least a portion of its top surface, its bottom surface, or both surfaces. The anterior portion, or trailing edge, of the implant is preferably generally greater in height than the opposing posterior portion, or leading edge. In other words, the trailing edge is taller than the leading edge. The posterior portion and lateral sides may also be generally smooth and highly radiused, thus allowing for easier implantation into the disc space. Thus, the posterior portion may have a blunt nosed profile. The anterior portion of the implant may preferably be configured to engage a delivery device, a driver, or other surgical tools. The anterior portion may also be substantially flat.

According to certain embodiments, the present invention provides an interbody spinal implant including a body having a top surface, a bottom surface, opposing lateral sides, opposing anterior and posterior portions, a substantially hollow center, and a single vertical aperture. The single vertical aperture extends from the top surface to the bottom surface, has a size and shape predetermined to maximize the surface area of the top surface and the bottom surface available proximate the anterior and posterior portions while maximizing both radiographic visualization and access to the substantially hollow center, and defines a transverse rim.

According to certain embodiments, the present invention provides an interbody spinal implant including a body having a top surface, a bottom surface, opposing lateral sides, and opposing anterior and posterior portions. At least a portion of the top surface, the bottom surface, or both surfaces has a roughened surface topography including both micro features and nano features, without sharp teeth that risk damage to bone structures, adapted to grip bone through friction generated when the implant is placed between two vertebrae and to inhibit migration of the implant. The roughened surface topography typically further includes macro features and the macro features, micro features, and nano features overlap.

The present invention also encompasses a process of fabricating a roughened surface topography on a surface of an implant. The process includes separate and sequential macro processing, micro processing, and nano processing steps.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 22 illustrates the parameters Ra, Rmax, and Sm for the completed macro and nano surface features of the implant according to an embodiment of the present invention;

DETAILED DESCRIPTION OF THE INVENTION

Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also facilitate osteointegration with the surrounding living bone.

Anterior interbody spinal implants in accordance with certain aspects of the present invention can be preferably made of a durable material such as stainless steel, stainless steel alloy, titanium, or titanium alloy, but can also be made of other durable materials such as, but not limited to, polymeric, ceramic, and composite materials. For example, certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the present invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 2:
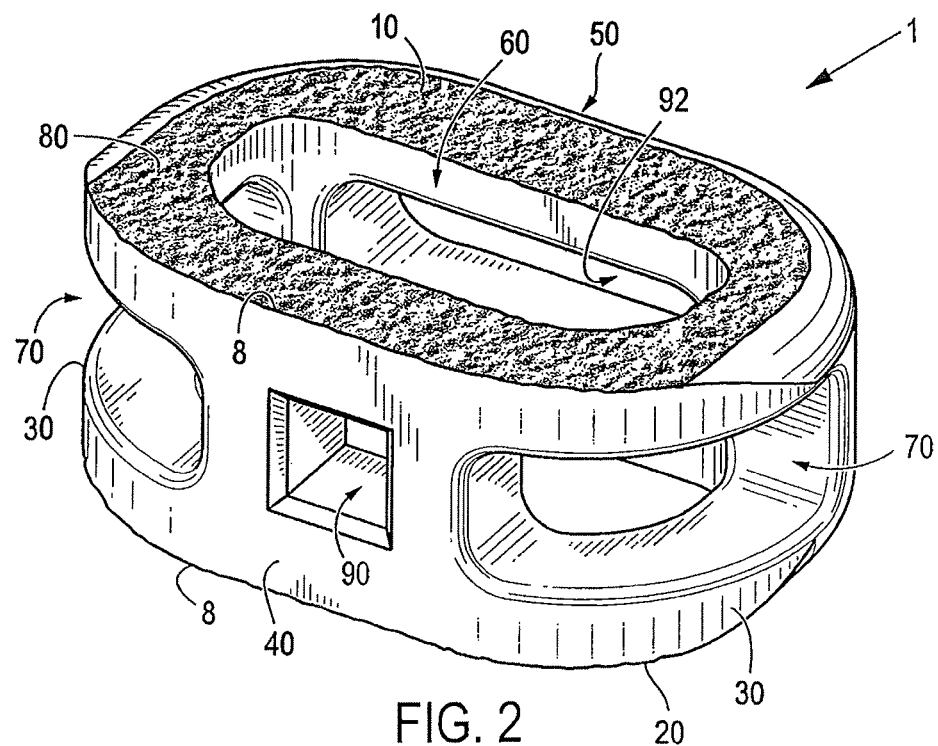
FIG. 2 shows a perspective view of a first embodiment of the interbody spinal implant having a generally oval shape and roughened surface topography on the top surface.

Referring now to the drawing, in which like reference numbers refer to like elements throughout the various figures that comprise the drawing, FIG. 2 shows a perspective view of a first embodiment of the interbody spinal implant 1 especially well adapted for use in an ALIF procedure. The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. Distinguish the roughened topography 80, however, from the disadvantageous teeth provided on the surfaces of some conventional devices.

Figure 3:
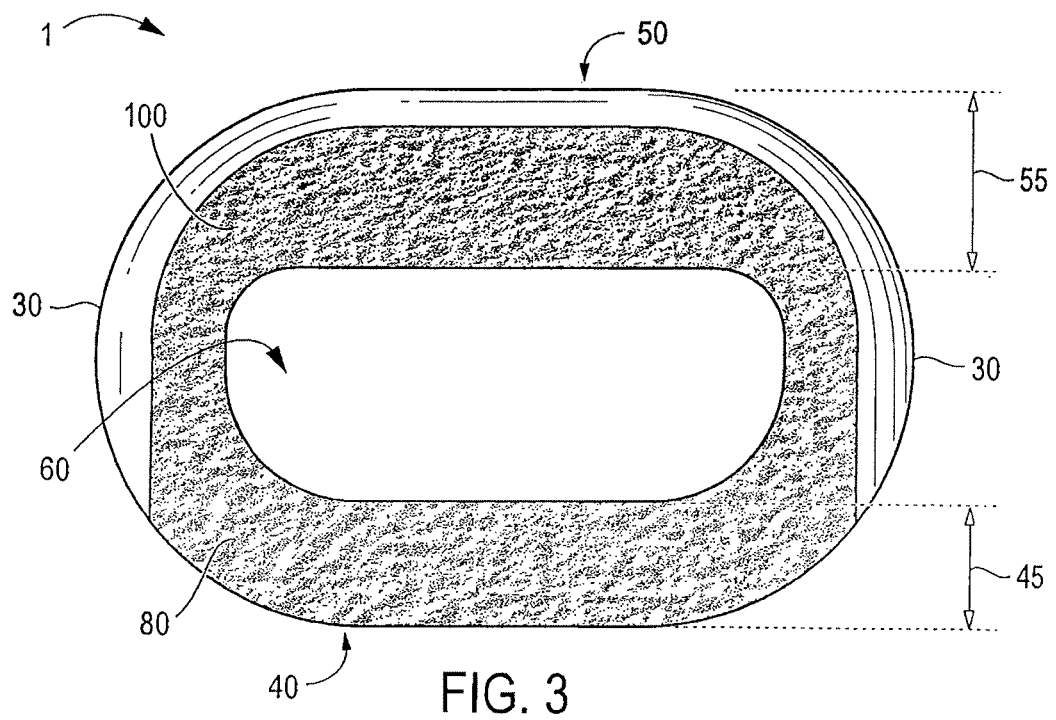
FIG. 3 depicts a top view of the first embodiment of the interbody spinal implant.

Certain embodiments of the interbody spinal implant 1 are substantially hollow and have a generally oval-shaped transverse cross-sectional area with smooth, rounded, or both smooth and rounded lateral sides and posterior-lateral corners. As used in this document, "substantially hollow" means at least about 33% of the interior volume of the interbody spinal implant 1 is vacant. The implant 1 includes at least one vertical aperture 60 that extends the entire height of the implant body. As illustrated in the top view of FIG. 3, the vertical aperture 60 further defines a transverse rim 100 having a greater posterior portion thickness 55 than an anterior portion thickness 45.

In at least one embodiment, the opposing lateral sides 30 and the anterior portion 40 have a rim thickness of about 5 mm, while the posterior portion 50 has a rim thickness of about 7 mm. Thus, the rim posterior portion thickness 55 may allow for better stress sharing between the implant 1 and the adjacent vertebral endplates and helps to compensate for the weaker posterior endplate bone. In certain embodiments, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (i.e., for the anterior portion thickness 45 to be substantially the same as the posterior portion thickness 55) or, in fact, for the posterior portion 50 to have a rim thickness less than that of the opposing lateral sides 30 and the anterior portion 40. Some studies have challenged the characterization of the posterior endplate bone as weaker.

Certain embodiments of the implant 1 are generally shaped to reduce the risk of subsidence, and improve stability, by maximizing contact with the apophyseal rim of the vertebral endplates. Embodiments may be provided in a variety of anatomical footprints having a medial-lateral width ranging from about 32 mm to about 44 mm. Interbody spinal implants, as now taught, generally do not require extensive supplemental or obstructive implant instrumentation to maintain the prepared disc space during implantation. Thus, the interbody spinal implant 1 and associated implantation methods, according to presently preferred aspects of the present invention, allow for larger sized implants as compared with the size-limited interbody spinal implants known in the art. This advantage allows for greater medial-lateral width and correspondingly greater contact with the apophyseal rim.

Figure 4:
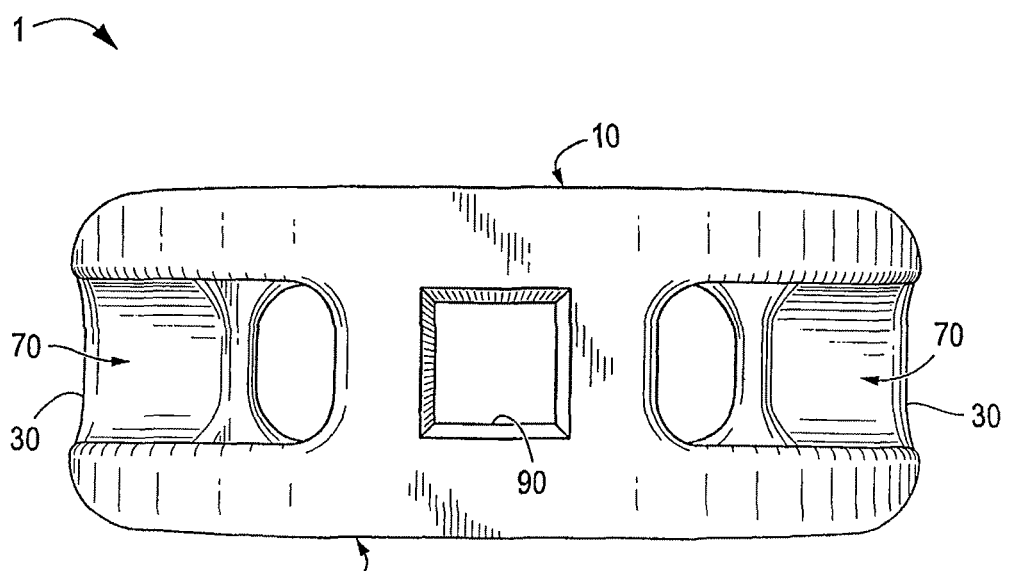
FIG. 4 depicts an anterior view of the first embodiment of the interbody spinal implant.
Figure 5:
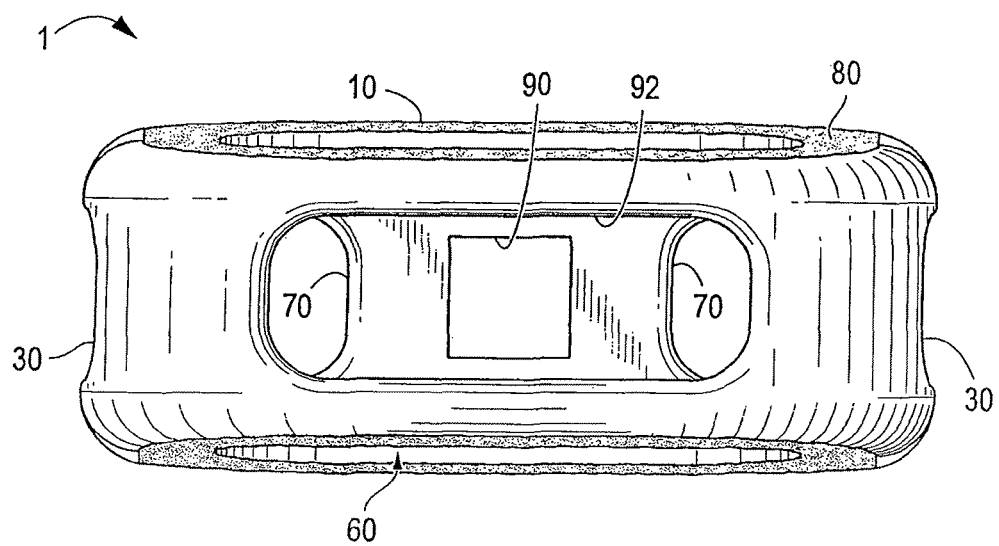
FIG. 5 depicts a posterior view of the first embodiment of the interbody spinal implant.

FIG. 4 depicts an anterior view, and FIG. 5 depicts a posterior view, of an embodiment of the interbody spinal implant 1. As illustrated in FIGS. 2 and 4, the implant 1 has an opening 90 in the anterior portion 40. As illustrated in FIGS. 4 and 5, in one embodiment the posterior portion 50 has a similarly shaped opening 90. In another embodiment, as illustrated in FIG. 2, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

Figure 7:
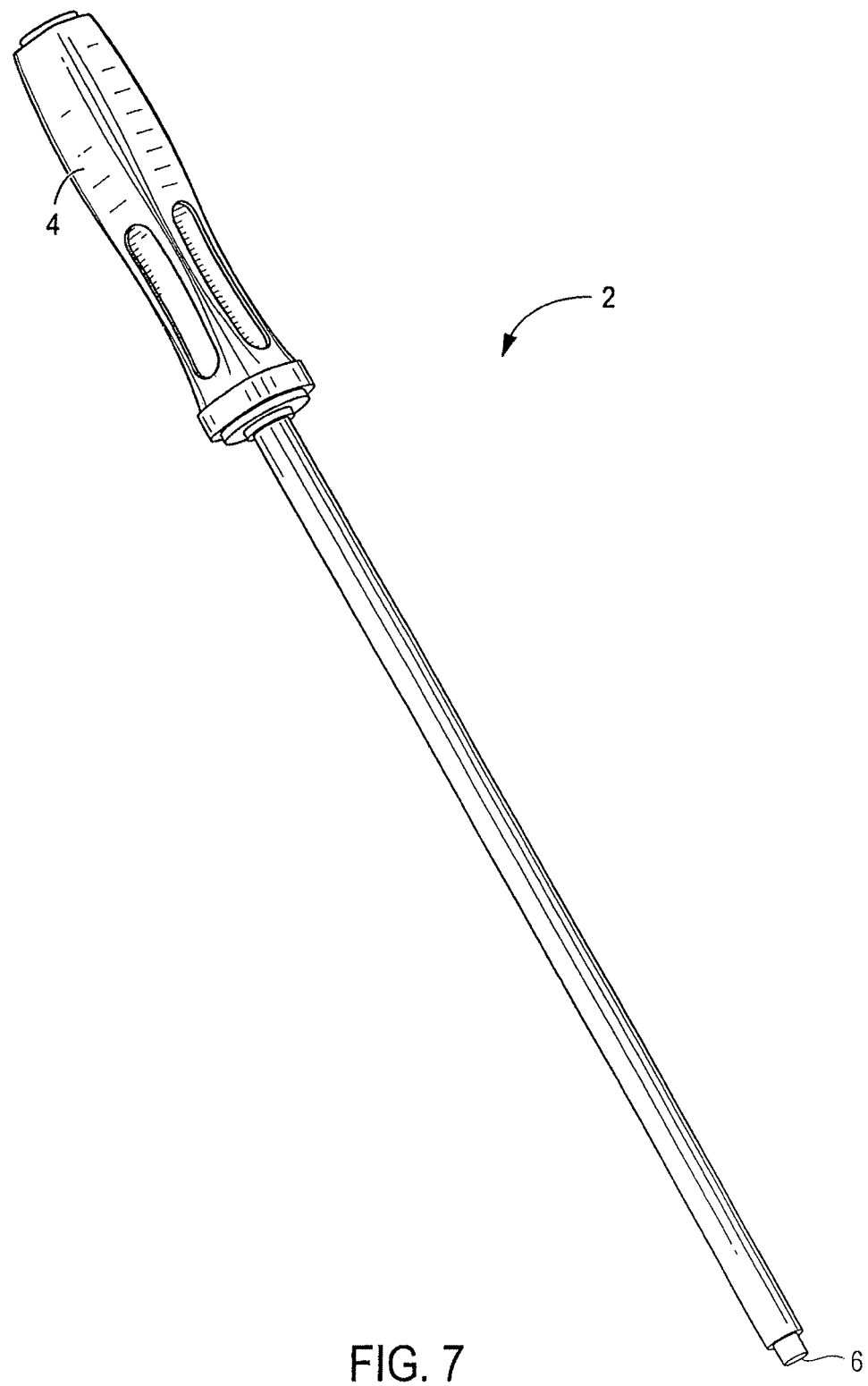
FIG. 7 shows an exemplary surgical tool (implant holder) to be used with certain embodiments of the interbody spinal implant.

FIG. 7 shows an exemplary surgical tool, specifically an implant holder 2, to be used with certain embodiments of the interbody spinal implant 1. Typically, the implant holder 2 has a handle 4 that the caretaker can easily grasp and an end 6 that engages the opening 90. The end 6 may be threaded to engage corresponding threads in the opening 90. The size and shape of the opening 90 can be varied to accommodate a variety of tools. Thus, although the opening 90 is substantially square as illustrated in FIGS. 2, 4, and 5, other sizes and shapes are feasible.

Figure 6A:
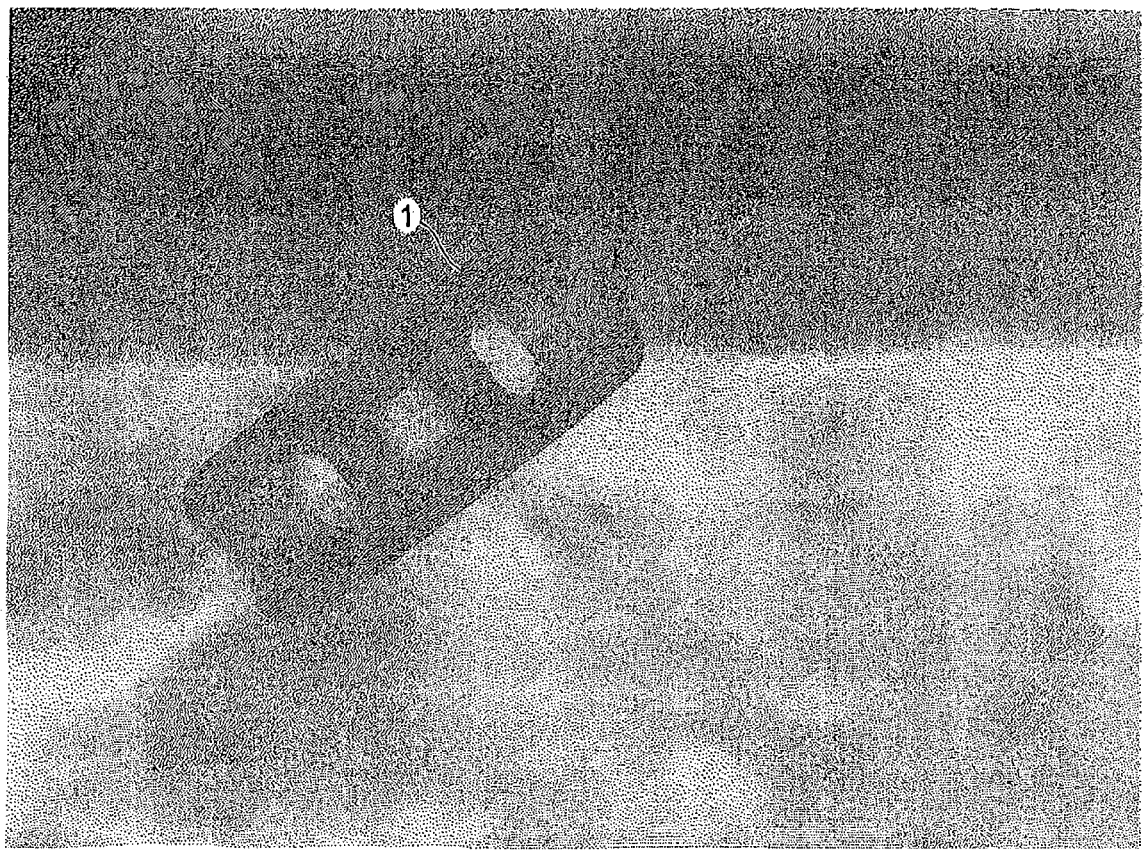
FIG. 6A depicts a first post-operative radiograph showing visualization of an embodiment of the interbody spinal implant.
Figure 6B:
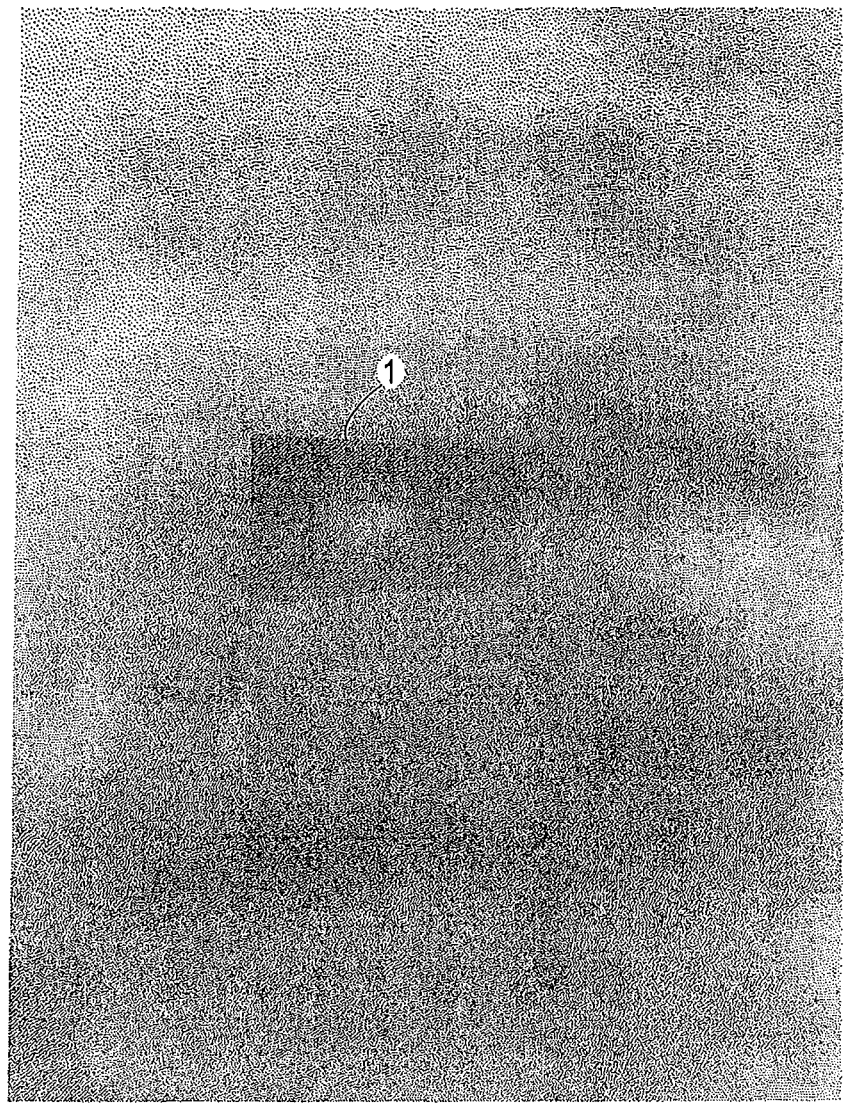
FIG. 6B depicts a second post-operative radiograph showing visualization of an embodiment of the interbody spinal implant.
Figure 6C:
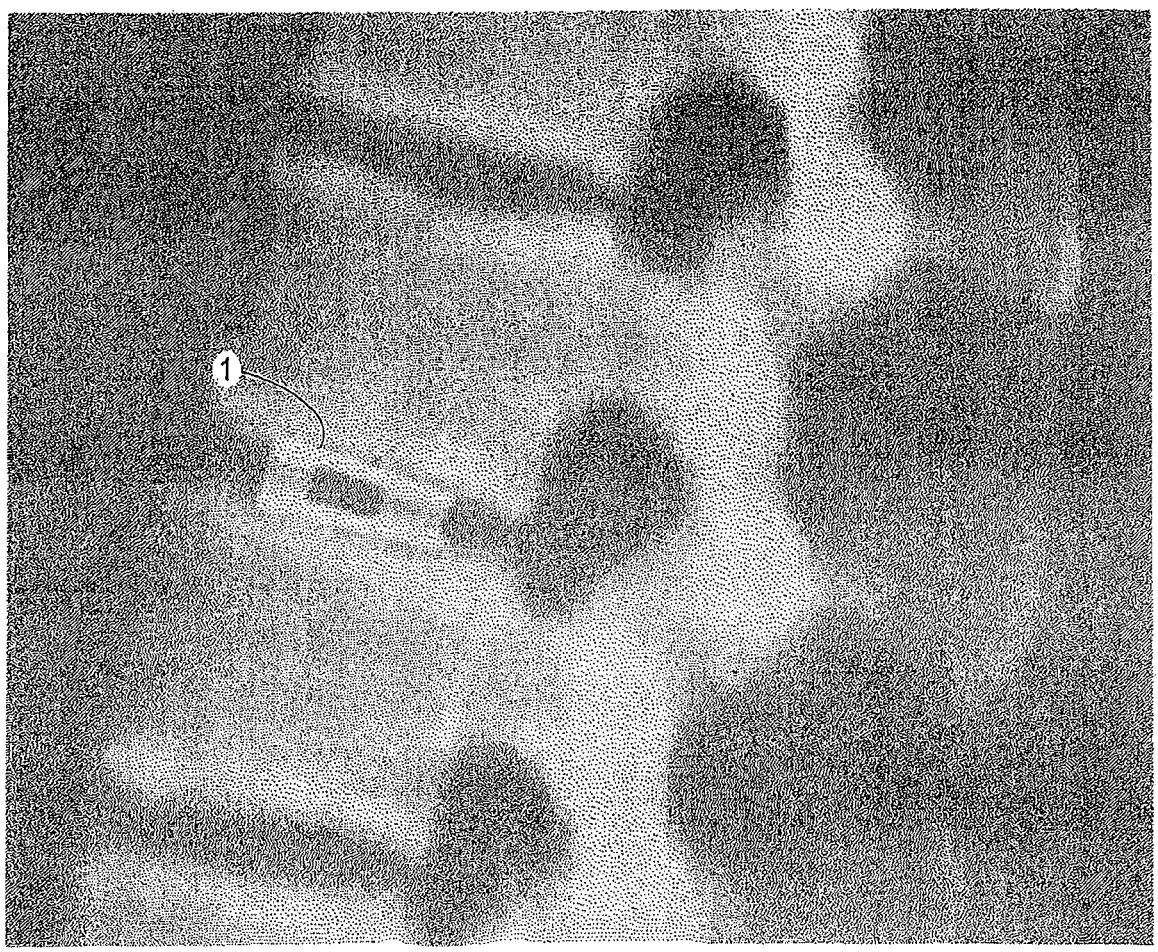
FIG. 6C depicts a third post-operative radiograph showing visualization of an embodiment of the interbody spinal implant.

The implant 1 may further include at least one transverse aperture 70 that extends the entire transverse length of the implant body. As shown in FIGS. 6A, 6B, and 6C, these transverse apertures 70 may provide improved visibility of the implant 1 during surgical procedures to ensure proper implant placement and seating, and may also improve post-operative assessment of implant fusion. Still further, the substantially hollow area defined by the implant 1 may be filled with cancellous autograft bone, allograft bone, DBM, porous synthetic bone graft substitute, BMP, or combinations of these materials (collectively, bone graft materials), to facilitate the formation of a solid fusion column within the spine of a patient.

The anterior portion 40, or trailing edge, of the implant 1 is preferably generally greater in height than the opposing posterior portion 50. Accordingly, the implant 1 may have a lordotic angle to facilitate sagittal alignment. The implant 1 may better compensate, therefore, for the generally less supportive bone found in the posterior regions of the vertebral endplate. The posterior portion 50 of the interbody implant 1, preferably including the posterior-lateral corners, may also be highly radiused, thus allowing for ease of implantation into the disc space. Thus, the posterior portion 50 may have a generally blunt nosed profile. The anterior portion 40 of the implant 1 may also preferably be configured to engage a delivery device, driver, or other surgical tool (and, therefore, may have an opening 90).

As illustrated in FIG. 2, the anterior portion 40 of the implant 1 is substantially flat. Thus, the anterior portion 40 provides a face that can receive impact from a tool, such as a surgical hammer, to force the implant 1 into position. The implant 1 has a sharp edge 8 where the anterior portion 40 meets the top surface 10, where the anterior portion 40 meets the bottom surface 20, or in both locations. The sharp edge or edges 8 function to resist pullout of the implant 1 once it is inserted into position.

Certain embodiments of the present invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. Interbody spinal implants 1, as now taught, are generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

The implant 1 further includes the roughened topography 80 on at least a portion of its top and bottom surfaces 10, 20 for gripping adjacent bone and inhibiting migration of the implant 1. In at least one embodiment, the interbody spinal implant 1 is formed of metal. In a more preferred embodiment, the implant 1 is comprised of titanium, or a titanium alloy, having the surface roughened topography 80. The surfaces of the implant 1 are preferably bioactive. An oxide layer naturally forms on titanium alloy. In a preferred embodiment, however, the base material of the implant 1 includes the elements Ti, Al, and V without any coatings.

In a specific embodiment of the present invention, the roughened topography 80 is obtained by combining separate macro processing, micro processing, and nano processing steps. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters. The term "nano" typically means one billionth ($10^{-9}$); for example, in the present application, dimensions measured in manometers (nm) which correspond to $10^{-9}$ meters.

Figure 1A:
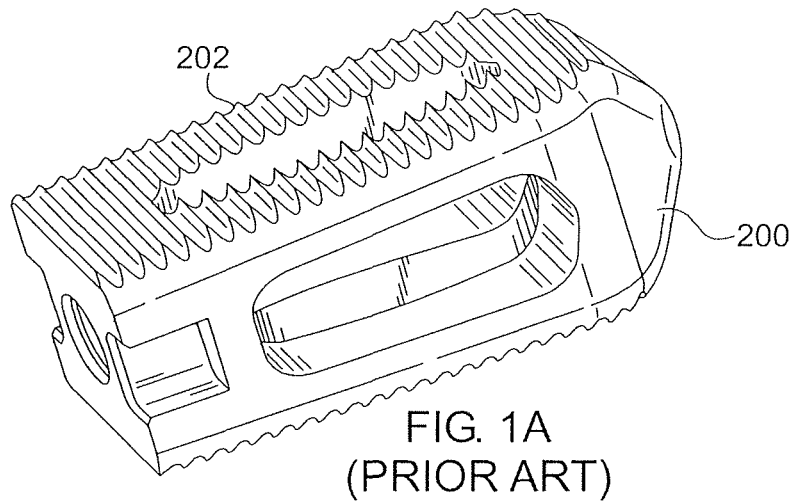
FIG. 1A is a perspective view of a traditional implant having sharp teeth on its top and bottom surfaces.
Figure 1B:
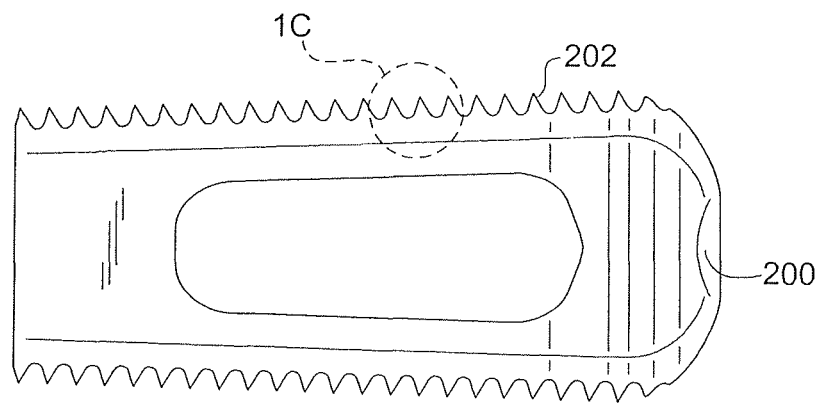
FIG. 1B is a side view of the traditional implant illustrated in FIG. 1A.
Figure 1C:
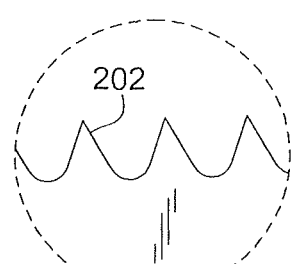
FIG. 1C is an expanded view of a portion of the traditional implant illustrated in FIG. 1B.
Figure 10A:
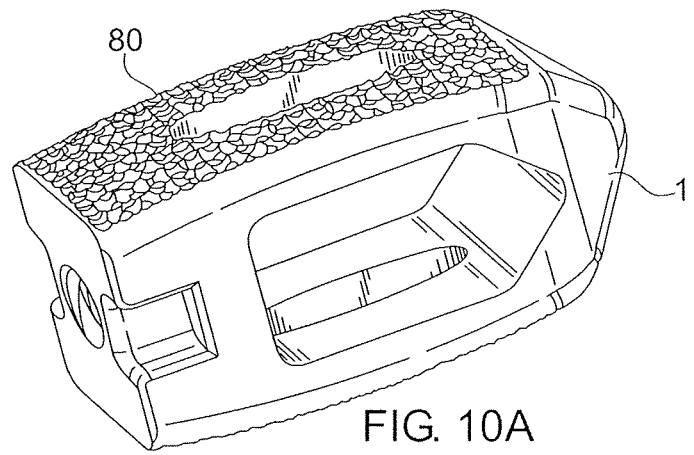
FIG. 10A is a perspective view of an implant having a roughened topography according to another embodiment of the present invention.
Figure 10B:
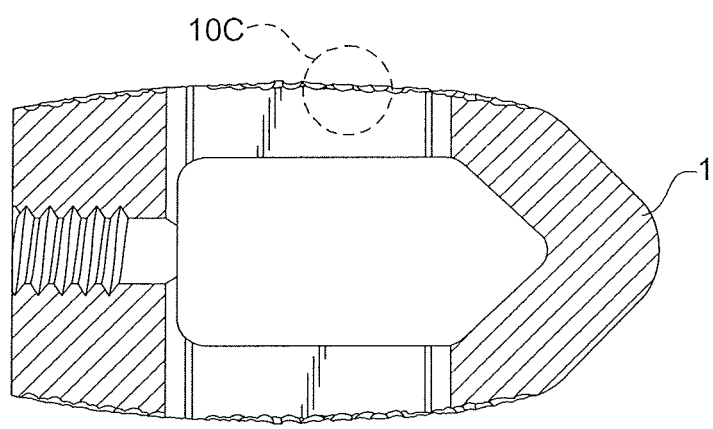
FIG. 10B is a side view of the implant illustrated in FIG. 10A.
Figure 10C:
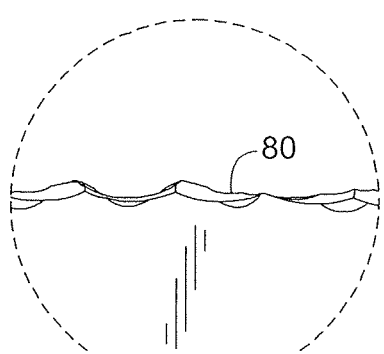
FIG. 10C is an expanded view of a portion of the implant illustrated in FIG. 10B.

FIGS. 10A, 10B, and 10C illustrate the interbody implant 1 with one embodiment of the roughened topography 80 according to the present invention. Specifically, FIG. 10A is a perspective view of the implant 1. FIG. 10B is a side view of the implant 1. And FIG. 1C is an expanded view of a portion of the implant 1 taken along the detail 10C illustrated in FIG. 1B, highlighting the pattern of the example embodiment of the roughened topography 80.

The interbody implant 1 has a roughened topography 80 with predefined surface features that (a) engage the vertebral endplates with a friction fit and, following an endplate preserving surgical technique, (b) attain initial stabilization, and (c) benefit fusion. The composition of the endplate is a thin layer of notch-sensitive bone that is easily damaged by features (such as teeth) that protrude sharply from the surface of traditional implants. Avoiding such teeth and the attendant risk of damage, the roughened topography 80 of the implant 1 does not have teeth or other sharp, potentially damaging structures; rather, the roughened topography 80 has a pattern of repeating features of predetermined sizes, smooth shapes, and orientations. By "predetermined" is meant determined beforehand, so that the predetermined characteristic of the implant 1 must be determined, i.e., chosen or at least known, before use of the implant 1.

The shapes of the frictional surface protrusions of the roughened topography 80 are formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding and thermal and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features when overlapping work to increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features are typically divided into three size scales: nano, micro, and macro. The overlapping of the three feature sizes can be achieved using manufacturing processes that are completed sequentially and, therefore, do not remove or degrade the previous method.

The first step in the process is either mechanical (e.g., machining though conventional processes) or chemical bulk removal to generate macro features, roughly spherical in shape without undercuts or protruding sharp edges. Other shapes are possible, such as ovals, polygons (including rectangles), and the like. These features are overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer dictates the final chemistry of the implant material.

Figure 23:
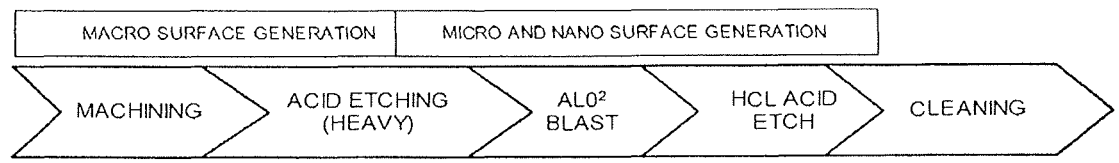
FIG. 23 illustrates one set of process steps that can be used to form macro, micro, or nano processes.

FIG. 23 illustrates one set of process steps that can be used to form an embodiment of the roughened topography 80 according to the present invention. As illustrated, there is some overlap in the processes that can be applied to form each of the three types of features (macro, micro, and nano). For example, acid etching can be used to form the macro features, then the same or a different acid etching process can be used to form the micro features.

The final and overall shapes and dimensions of the features of the roughened topography 80 of the implant 1 are balanced to achieve design goals. More specifically, the combination of a rough but not sharp surface and the atraumatic surgical procedure generates initial stabilization upon insertion of the implant 1 into the vertebral space. As healing begins, the tissue cells benefit from this combination and can more rapidly anchor the implant 1 in a growing bone or fusion. Focusing high loads in small areas is also known through Wolff's Law to cause remodeling of the osseous tissues where they dissolve under high loads.

Wolff's law is a theory developed by the German anatomist and surgeon Julius Wolff in the 19th century. The theory states that bone in a healthy person or animal will adapt to the loads under which the bone is placed. If loading on a particular bone increases, the bone will remodel itself over time to become stronger to resist that loading. The internal architecture of the trabeculae undergoes adaptive changes, followed by secondary changes to the external cortical portion of the bone, perhaps becoming thicker as a result. The converse is true as well: if the loading on a bone decreases, the bone will become weaker due to turnover. It is less metabolically costly to maintain the bone and there is no stimulus for continued remodeling that is required to maintain bone mass.

This remodeling can work against the goal of fusion both biologically and mechanically with the implant 1 if the contact points are too aggressive, having points or sharp edges that focus loading of the bone and cause stress-induced necrosis or resorbtion of the bone tissues. In contrast, overly smooth surfaces do not have the benefit of generating enough initial friction for the interbody device to stabilize and allow for fusion. The improved surface of the roughened topography 80 of the implant 1, the related design of the surgical instruments used to insert the implant 1, and the procedure for conducting surgery work in concert to generate sufficient frictional resistance to biological forces allowing for beneficial initial stabilization and rapid long-term fusion of the joint to the implant 1. Instruments and procedures are balanced between preparing the surgical site with an endplate-preserving procedure and allowing for an implant 1 with a roughened top and bottom surface to frictionally fit into the site.

The macro features of the roughened topography 80 are relatively large machined or etched features preferably, although not necessarily, organized in regular repeating patters and overlapping each other. The macro features also are cut from the base material that was used to form the implant 1. In a preferred process, the macro features are formed in three, sequential steps.

Figure 11A:
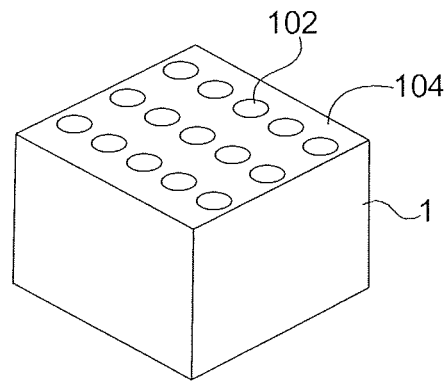
FIG. 11A is a perspective view illustrating the result of a first step in forming the macro features of the roughened topography of the implant according to one embodiment of the present invention.

FIG. 11A illustrates the result of the first step in forming the macro features. Specifically, a first cut pattern 102 of the macro features is formed in a surface (i.e., in the top surface 10 or the bottom surface 20) of the implant 1. The "cut 1" features of the first cut pattern 102 cover about 20% of the total area of the surface, leaving about 80% of the original surface 104 remaining. The range of these percentages is about ±20%.

Figure 12A:
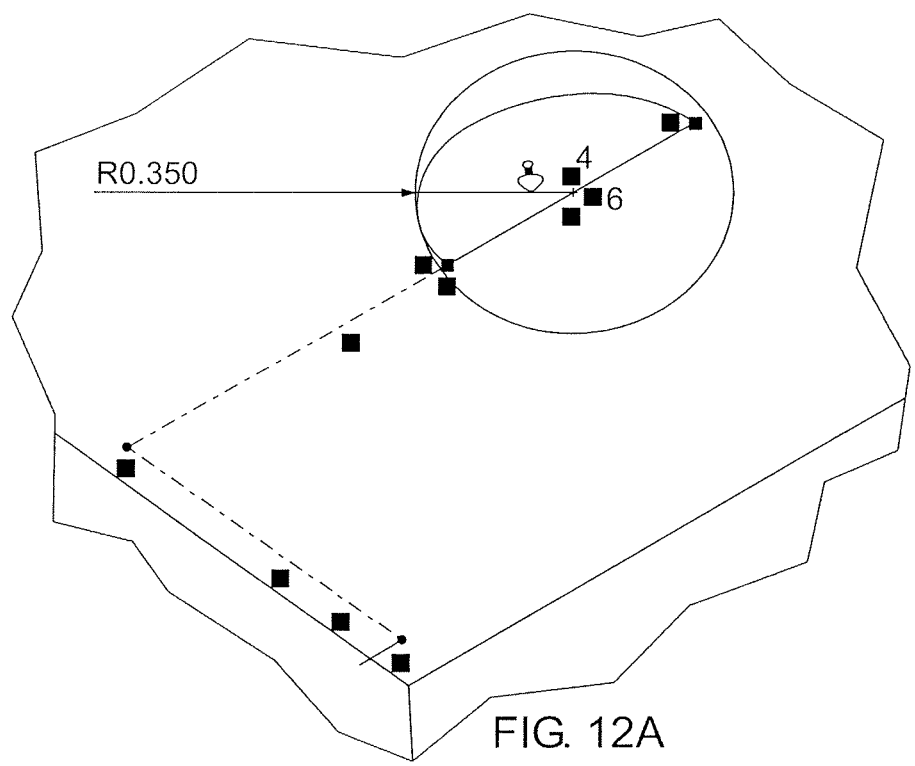
FIG. 12A is a perspective, simulated view of the implant following completion of a first process step in forming the macro features of the roughened topography of the implant according to one embodiment of the present invention, highlighting the diameter of the feature.
Figure 12B:
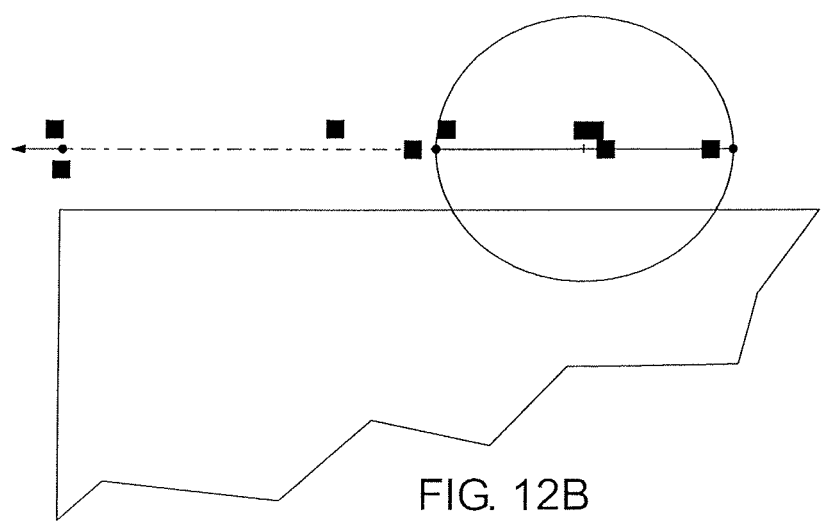
FIG. 12B is a side view corresponding to the perspective view of FIG. 12A.
Figure 13A:
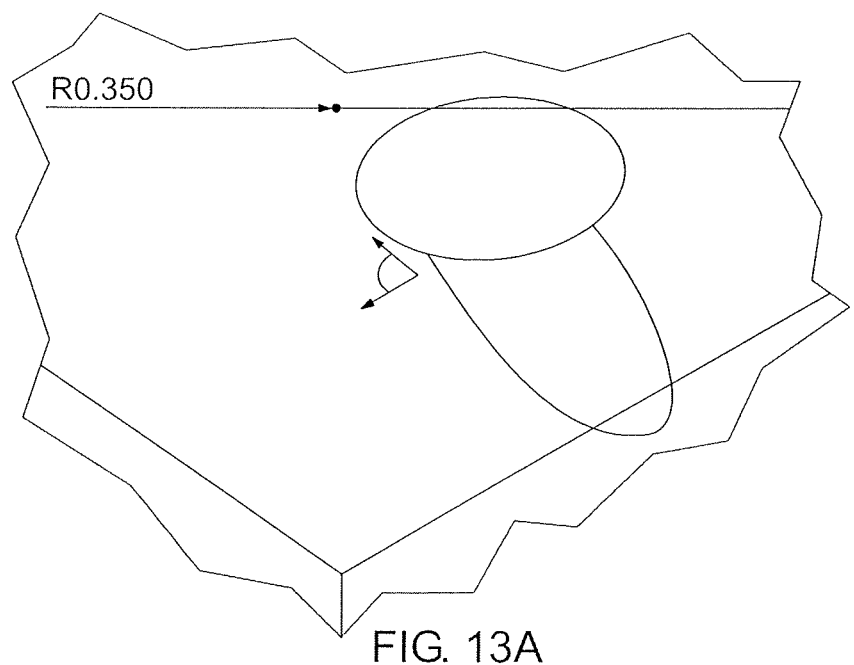
FIG. 13A is a perspective, simulated view of the implant following completion of a first process step in forming the macro features of the roughened topography of the implant according to one embodiment of the present invention, highlighting the edges of the feature.
Figure 13B:
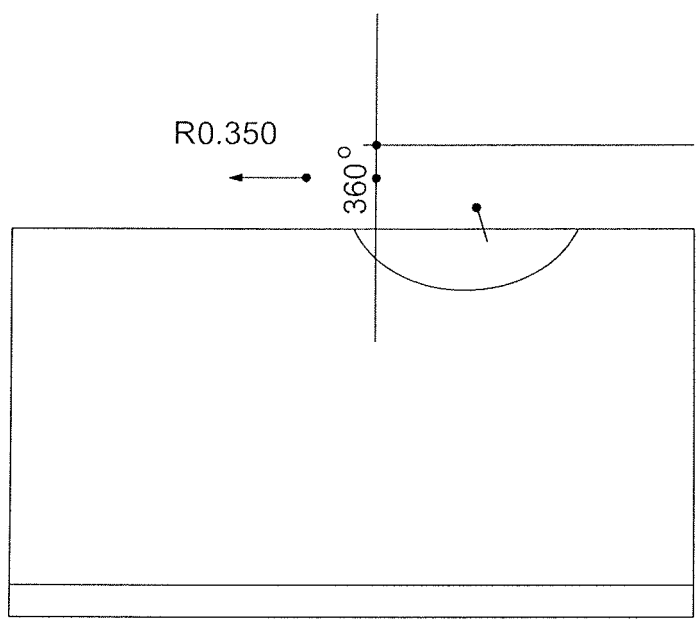
FIG. 13B is a side view corresponding to the perspective view of FIG. 13A.
Figure 14A:
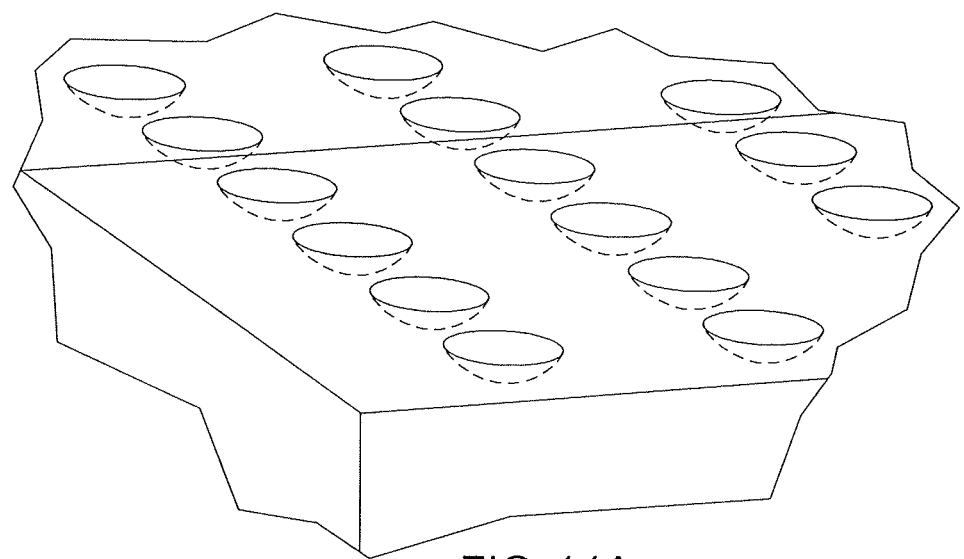
FIG. 14A is a perspective, simulated view of the implant following completion of a first process step in forming the macro features of the roughened topography of the implant according to one embodiment of the present invention, highlighting the pattern of repeating features.
Figure 14B:
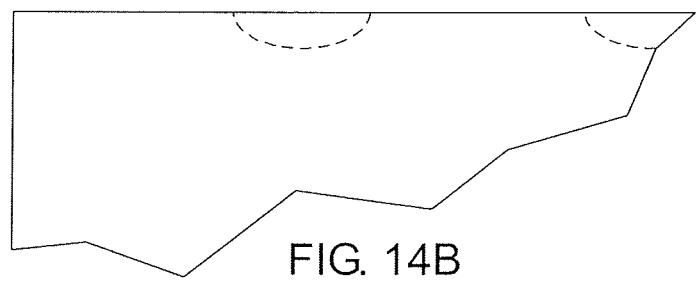
FIG. 14B is a side view corresponding to the perspective view of FIG. 14A.

FIG. 12A is a perspective view, and FIG. 12B is a side view, of a cut 1 feature. FIG. 13A is a perspective view, and FIG. 13B is a side view, highlighting the edges of a cut 1 feature. As shown, the "cut 1" features of the first cut pattern 102 do not have any undercuts. These "cut 1" features have the smallest diameter and greatest depth of the macro features that are formed during the sequential steps. FIG. 14A is a perspective view, and FIG. 14B is a side view, showing an example regular and repeating pattern of the cut 1 features that form the first cut pattern 102. See also FIG. 11A.

Figure 11B:
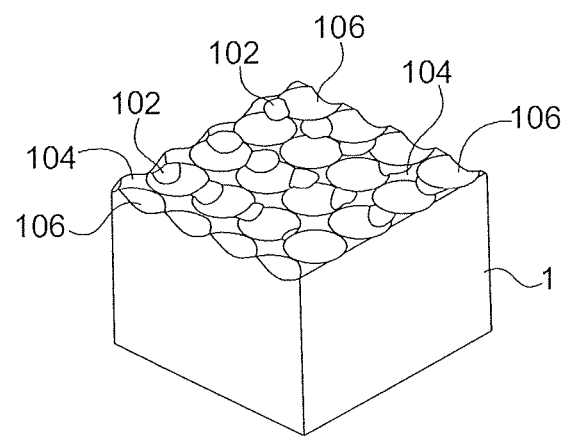
FIG. 11B is a perspective view illustrating the result of a second step in forming the macro features of the roughened topography of the implant according to one embodiment of the present invention.

FIG. 11B illustrates the result of the second step in forming the macro features. Specifically, a second cut pattern 106 of the macro features is formed in the surface of the implant 1. Together, the "cut 1" features of the first cut pattern 102 and the "cut 2" features of the second cut pattern 106 cover about 85% of the total area of the surface, leaving about 15% of the original surface 104 remaining. The range of these percentages is about ±10%. These "cut 2" features have both a diameter and a depth between those of the "cut 1" and "cut 3" features of the macro features that are formed during the first and third steps of the process of forming the macro features of the roughened topography 80.

Figure 11C:
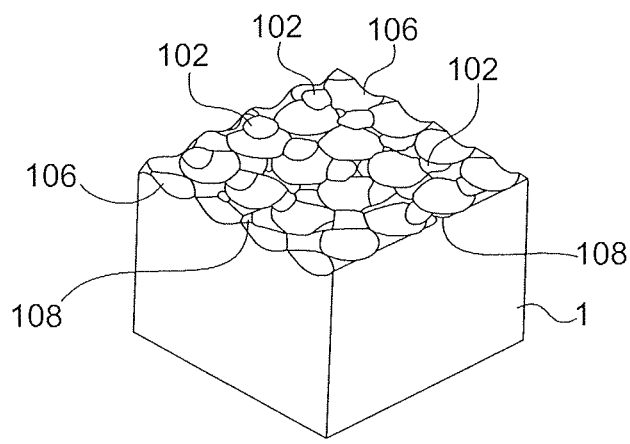
FIG. 11C is a perspective view illustrating the result of a third step in forming the macro features of the roughened topography of the implant according to one embodiment of the present invention.

FIG. 11C illustrates the result of the third and final step in forming the macro features. Specifically, a third cut pattern 108 of the macro features is formed in the surface of the implant 1. Together, the "cut 1" features of the first cut pattern 102, the "cut 2" features of the second cut pattern 106, and the "cut 3" features of the third cut pattern 108 cover about 95% of the total area of the surface, leaving about 5% of the original surface 104 remaining. The range of these percentages is about ±1%. These "cut 3" features have the largest diameter and least depth of the macro features that are formed during the sequential process steps.

Figure 15A:
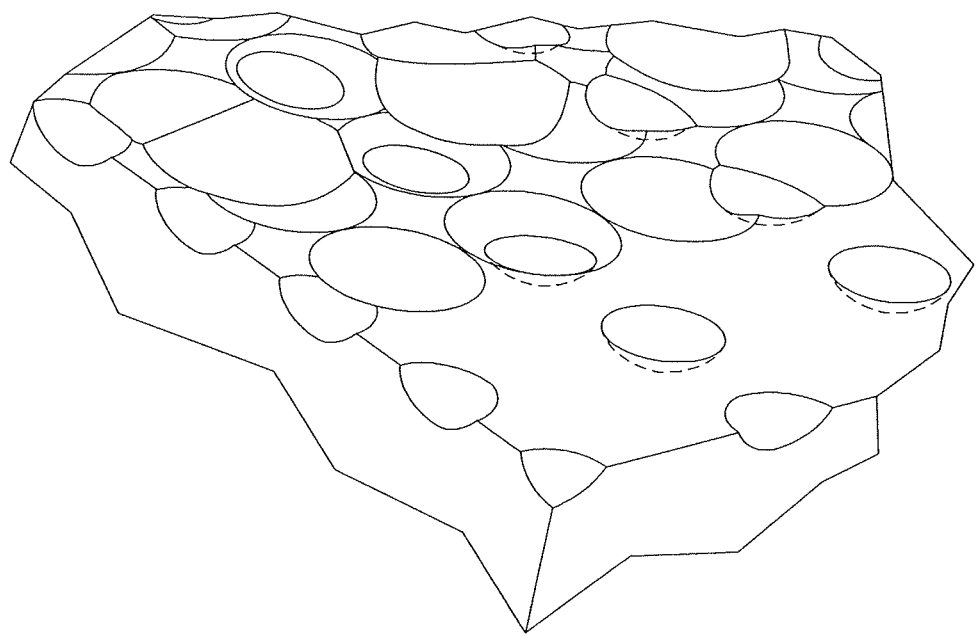
FIG. 15A is a perspective, simulated view of the implant following completion of the three process steps in forming the macro features of the roughened topography of the implant according to one embodiment of the present invention.
Figure 15B:
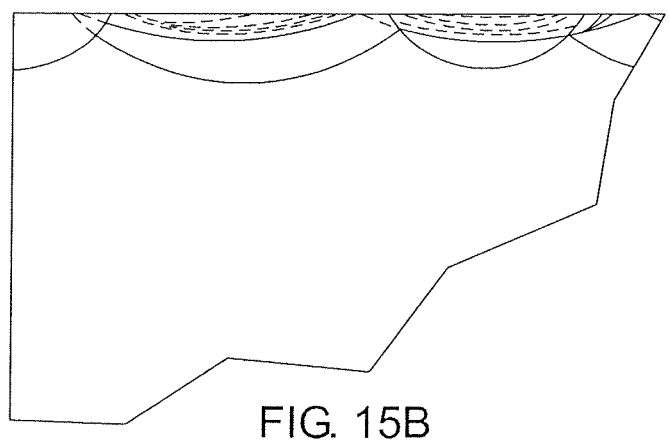
FIG. 15B is a side view corresponding to the perspective view of FIG. 15A.
Figure 16:
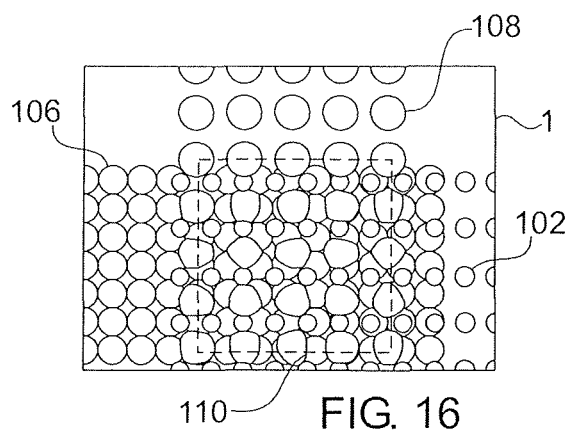
FIG. 16 is a top, simulated view showing each of the first cut pattern, the second cut pattern, and the third cut pattern individually and, in an area of overlapping features, the roughened topography following completion of the three, sequential processing steps and combining (in an overlapping pattern) the first cut pattern, the second cut pattern, and the third cut pattern of the macro features.
Figure 17:
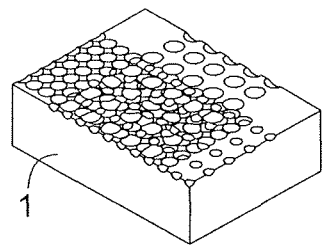
FIG. 17 is a perspective view of the implant illustrated in FIG. 16.

FIG. 15A is a perspective view, and FIG. 15B is a side view, of the macro features of the roughened topography 80 following completion of the three, sequential processing steps. As shown, the finished macro features comprise multiple patterns of the three, overlapping cuts: the first cut pattern 102, the second cut pattern 106, and the third cut pattern 108. FIG. 16 is a top, simulated view of the roughened topography 80 showing each of the first cut pattern 102, the second cut pattern 106, and the third cut pattern 108 individually and, in an area of overlapping features 110, the roughened topography 80 following completion of the three, sequential processing steps and combining (in an overlapping pattern) the first cut pattern 102, the second cut pattern 106, and the third cut pattern 108. FIG. 17 is a perspective view of the implant illustrated in FIG. 16.

Figure 18:
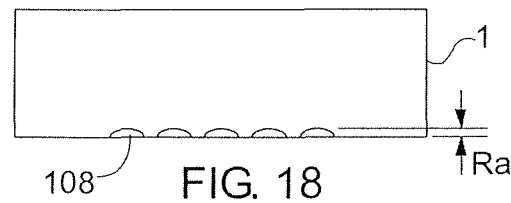
FIG. 18 is a side view illustrating the measurement of the average amplitude, Ra, for the third cut pattern of the implant shown in FIGS. 16 and 17.
Figure 19A:
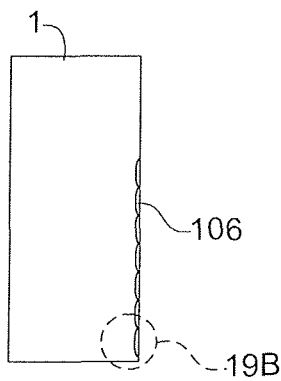
FIG. 19A is another side view of the implant shown in FIGS. 16 and 17.
Figure 20A:
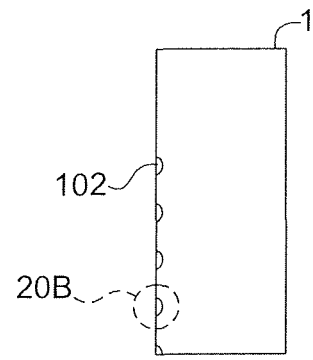
FIG. 20A is yet another side view of the implant shown in FIGS. 16 and 17.
Figure 19B:
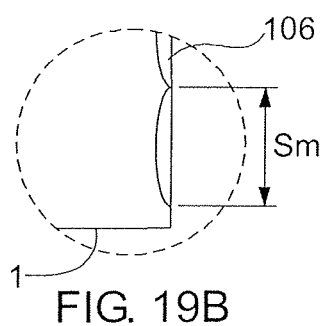
FIG. 19B is an expanded view of a portion of the implant illustrated in FIG. 19A illustrating the measurement of the mean spacing, Sm, for the second cut pattern.
Figure 20B:
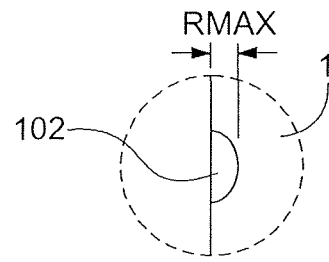
FIG. 20B is an expanded view of a portion of the implant illustrated in FIG. 20A illustrating the measurement of the maximum peak-to-valley height, Rmax, for the first cut pattern.
Figure 21:
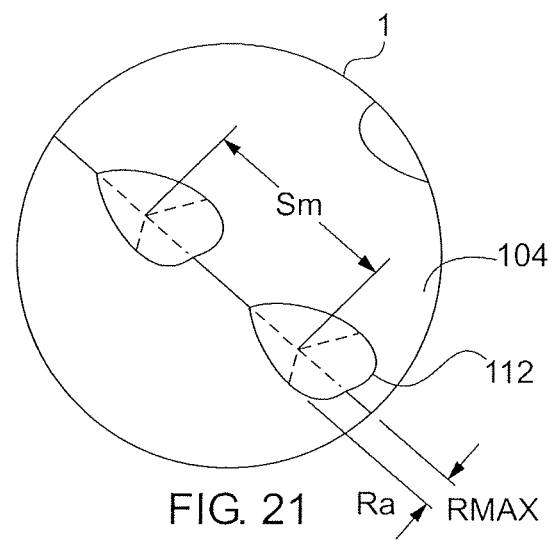
FIG. 21 illustrates three parameters, namely, Ra, Rmax, and Sm, used to measure surface roughness for the macro features of an implant.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Meanwhile, FIG. 18 is a side view illustrating the measurement of Ra for the third cut pattern 108 of the implant 1 shown in FIGS. 16 and 17. FIG. 19A is another side view of the implant 1 shown in FIGS. 16 and 17, and FIG. 19B is an expanded view of a portion of the implant 1 illustrated in FIG. 19A illustrating the measurement of Sm for the second cut pattern 106. FIG. 20A is yet another side view of the implant 1 shown in FIGS. 16 and 17, and FIG. 20B is an expanded view of a portion of the implant 1 shown in FIG. 20A illustrating the measurement of Rmax for the first cut pattern 102. FIG. 21 illustrates all three parameters, namely, Ra, Rmax, and Sm, for the macro features 112 of the implant 1.

After the macro features 112 are formed in the implant 1, additional process steps are sequentially applied to the implant 1, in turn, to form the micro and the nano surface features of the roughened topography 80. After the micro features are formed, less than about 3% of the original surface 104 remains. The range of that percentage is about ±1%. After the nano features are formed, the roughened topography 80 covers substantially all of the top surface 10, the bottom surface 20, or both surfaces of the implant 1. In a preferred embodiment, the entire implant 1 is dipped in an etchant bath (without any masks) so that the roughened topography 80 covers substantially all surfaces of the implant 1.

FIG. 22 illustrates the parameters Ra, Rmax, and Sm for the completed macro and nano surface features of the implant 1. As should be readily apparent to a skilled artisan, the process steps can be adjusted to create a mixture of depths, diameters, feature sizes, and other geometries suitable for a particular implant application. The orientation of the pattern of features can also be adjusted. Such flexibility is desirable, especially because the ultimate pattern of the roughened topography 80 of the implant 1 should be oriented in opposition to the biologic forces on the implant 1 and to the insertion direction. In one particular embodiment, for example, the pattern of the roughened topography 80 is modeled after an S-shaped tire tread.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 24:
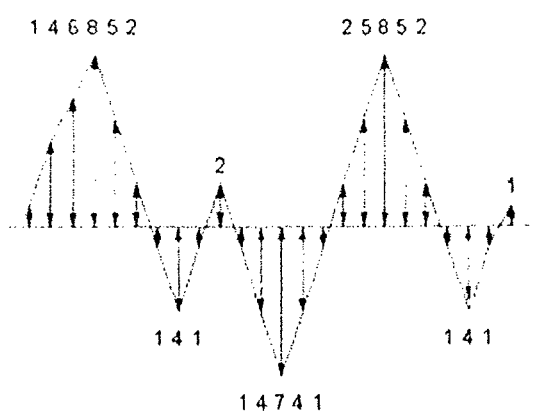
FIG. 24 graphically represents the average amplitude, Ra.

In practice, "Ra" is the most commonly used roughness parameter. It is the arithmetic average height. Mathematically, Ra is computed as the average distance between each roughness profile point and the mean line. In FIG. 24, the average amplitude is the average length of the arrows.

In mathematical terms, this process can be represented as $$Ra = \frac{1}{n}\sum_{i=1}^{n} |y_i|$$

2. Average Peak-to-Valley Roughness Rz

Figure 25:
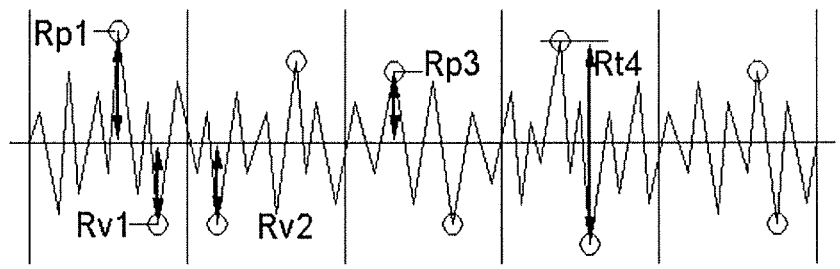
FIG. 25 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 25.

3. Maximum Peak-to-Valley Height Rmax

Figure 26:
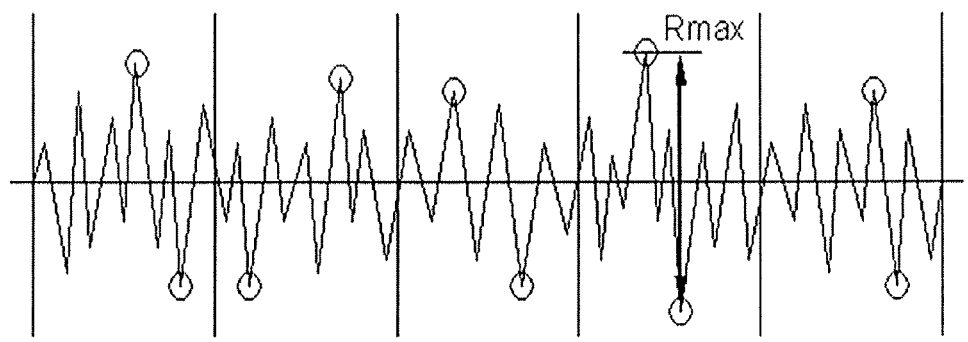
FIG. 26 graphically represents the maximum peak-to-valley height, Rmax.

The maximum peak-to-valley height, Rmax, is the maximum peak-to-valley distance in a single sampling length—as illustrated in the FIG. 26.

4. Total Peak-to-Valley of Waviness Profile Wt

Figure 27:
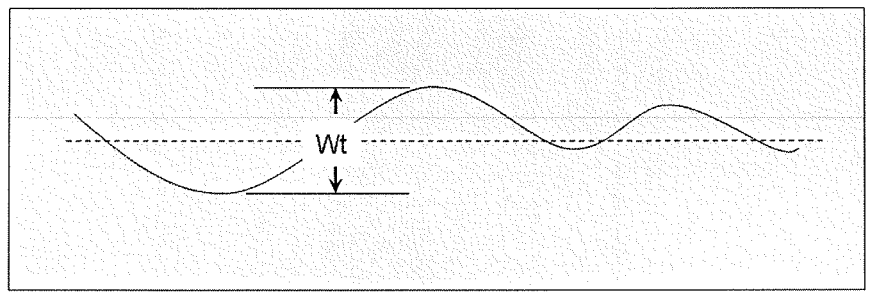
FIG. 27 graphically represents the total peak-to-valley of waviness profile.

The total peak-to-valley of waviness profile (over the entire assessment length) is illustrated in FIG. 27.

5. Mean Spacing Sm

Figure 28:
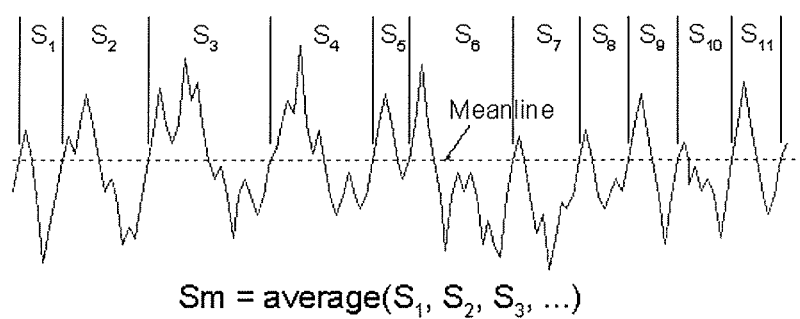
FIG. 28 graphically represents the mean spacing, Sm.

The mean spacing, Sm, is the average spacing between positive mean line crossings. The distance between each positive (upward) mean line crossing is determined and the average value is calculated, as illustrated in FIG. 28.

The parameters Sm, Rmax, and Ra can be used define the surface roughness following formation of each of the three types of features macro, micro, and nano. Such data are provided in Table 1 below.

TABLE 1

EXAMPLE DATA BY PROCESS STEP

| | Size (Sm) | Depth (Rmax) | Roughness (Ra) |
|---|---|---|---|
| Surface Feature Size and Roughness (Metric) Macro (µm) | | | |
| Max. | 2,000 | 500 | 200 |
| Min. | 400 | 40 | 20 |
| Avg. | 1,200 | 270 | 110 |
| Surface Feature Size and Roughness (Metric) Micro (µm) | | | |
| Max. | 400 | 40 | 20 |
| MM. | 20 | 2 | 1 |
| Avg. | 210 | 11 | 5.5 |
| Surface Feature Size and Roughness (Metric) Nano (µm) | | | |
| Max. | 20 | 2 | 1 |
| Min. | 0.5 | 0.2 | 0.01 |
| Avg. | 10.25 | 1.1 | 0.505 |

From the data in Table 1, the following preferred ranges (all measurements in microns) can be derived for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 20-200, with a range of 50-150 preferred and a range of 100-125 most preferred.

The following preferred ranges (all measurements in microns) can be derived for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, with a range of 2-15 preferred and a range of 4-10 most preferred.

The following preferred ranges (all measurements in microns) can be derived for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-1, with a range of 0.02-0.8 preferred and a range of 0.03-0.6 most preferred.

Certain embodiments of the implant 1 are generally shaped (i.e., made wide) to maximize contact with the apophyseal rim of the vertebral endplates. They are designed to be impacted between the endplates, with fixation to the endplates created by an interference fit and annular tension. Thus, the implant 1 is shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implant 1 to help restore cervical balance.

When endplate-sparing spinal implant 1 seats in the disc space against the apophyseal rim, it should still allow for deflection of the endplates like a diaphragm. This means that, regardless of the stiffness of the spinal implant 1, the bone graft material inside the spinal implant 1 receives load, leading to healthy fusion. The vertical load in the human spine is transferred though the peripheral cortex of the vertebral bodies. By implanting an apophyseal-supporting inter-body implant 1, the natural biomechanics may be better preserved than for conventional devices. If this is true, the adjacent vertebral bodies should be better preserved by the implant 1, hence reducing the risk of adjacent segment issues.

In addition, the roughened topography 80 of the top surface 30 and the bottom surface 40, along with the broad surface area of contact with the end-plates, is expected to yield a high pull-out force in comparison to conventional designs. As enhanced by the sharp edges 8, a pull-out strength of up to 3,000 newtons may be expected. The roughened topography 80 creates a biological bond with the end-plates over time, which should enhance the quality of fusion to the bone. Also, the in-growth starts to happen much earlier than the bony fusion. The center of the implant 1 remains open to receive bone graft material and enhance fusion. Therefore, it is possible that patients might be able to achieve a full activity level sooner than for conventional designs.

The spinal implant 1 according to the present invention offers several advantages relative to conventional devices. Such conventional devices include, among others, ring-shaped cages made of allograft bone material, threaded titanium cages, and ring-shaped cages made of PEEK or carbon fiber.

EXAMPLE SURGICAL METHODS

The following examples of surgical methods are included to more clearly demonstrate the overall nature of the invention. These examples are exemplary, not restrictive, of the invention.

Although removing the soft tissues of the diseased or damaged intervertebral disc is important for placement of the interbody fusion implant 1 so that the implant 1 primarily contacts the outer rim where vertebral discs are strongest, perforation or damage to the endplate can have degenerative effects to its healing after completion of the surgical procedure. Instrumentation used to remove the soft tissues is commonly known in the practice of orthopedic medicine, but the disc-preparation instruments used in connection with the implant 1 of the present invention are specifically designed and used in a prescribed method and aid in preserving the endplate structure.

Once the soft tissues have been exposed, a rasp 14 with a specific tooth design is used to remove only the soft tissues remaining adhered to the endplate surface. The goal of the disc preparation with the rasp 14 is to allow for an implant 1 of sufficient size to be implanted with as close an approximation in shape to the site primarily on the above-described apophyseal rim, the strongest structural area of the vertebral body. The design of the teeth of the rasp 14 is not so aggressive as to allow for easy bone removal but will capture fragments of the soft tissue and remove such fragments from the implantation site.

Figure 8:
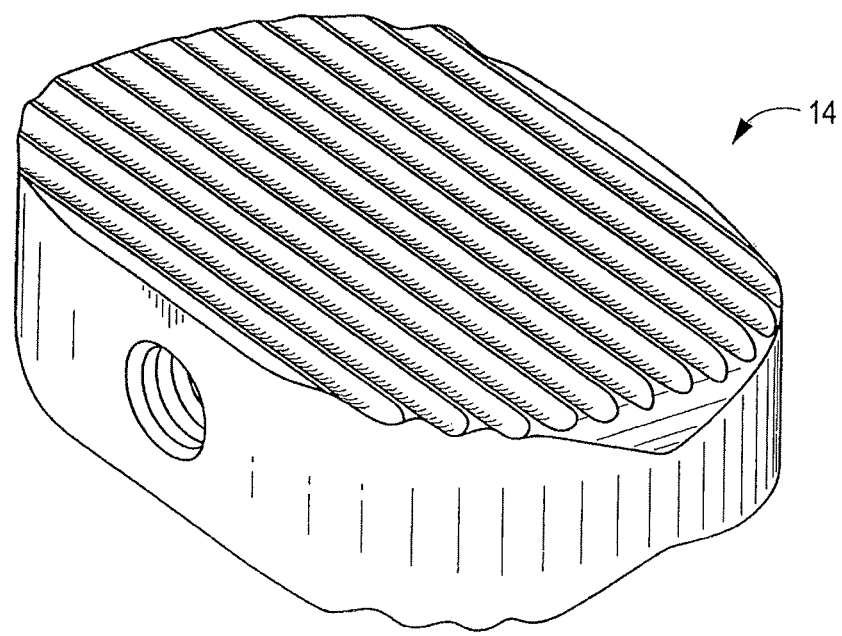
FIG. 8 shows an exemplary rasp used during certain methods of implantation.

FIG. 8 shows an exemplary rasp 14 used during certain methods of implantation. Typically, either a 32 mm or a 36 mm rasp 14 is used. A single rasp 14 is used to remove a minimal amount of bone. A lateral c-arm fluoroscopy can be used to follow insertion of the rasp 14 in the posterior disc space. The smallest height rasp 14 that touches both endplates (e.g., the superior and inferior endplates) is first chosen. After the disc space is cleared of all soft tissue and cartilage, distraction is then accomplished by using distractors (also called implant trials or distraction plugs). It is usually possible to distract 2-3 mm higher than the rasp 14 that is used because the disc space is elastic.

Use of a size-specific rasp 14, as shown in FIG. 8, preferably minimizes removal of bone, thus minimizing impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

The next step in the procedure is to place a smooth-surfaced sizing instrument between the vertebrae and determine the height size of the required implant for the patient. Implantation of a fusion implant to stop the advance of a malady must not allow for the movement of the vertebrae relative to each other during both short-term and long-term healing. Early in the healing process, when the load transfer serves the purpose of loading a captured amount of bone growth enhancement materials within the implant 1, the stability of the implant 1 in the surgically implanted position is balanced with a frictional surface of sufficient surface area to absorb loading without this surface acting to abrade or damage the critical endplate of the vertebra.

Figure 9:
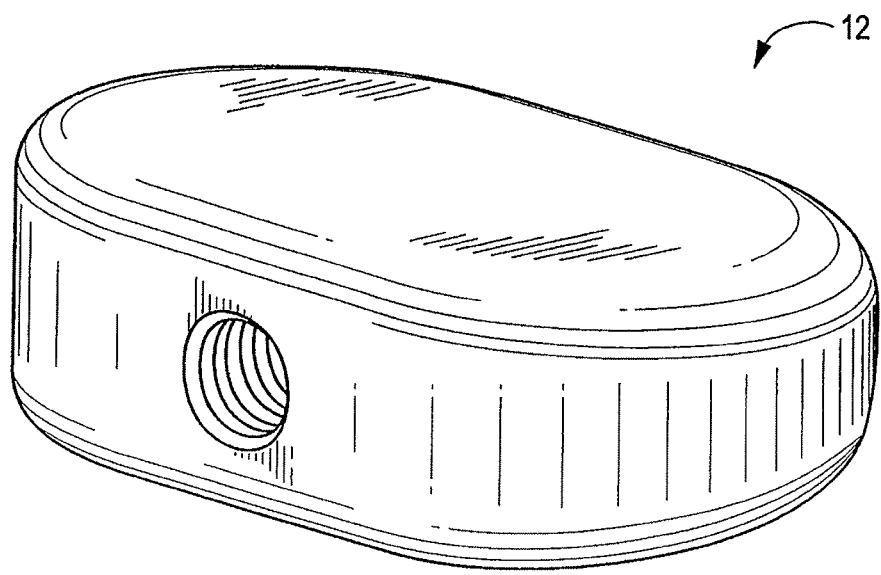
FIG. 9 shows an exemplary distractor used during certain methods of implantation.

FIG. 9 shows an exemplary distractor 12 used during certain methods of implantation. The implant trials, or distractors 12, are solid polished blocks which have a peripheral geometry identical to that of the implant 1. These distractor blocks may be made in various heights to match the height of the implant 1. The disc space is adequately distracted by sequentially expanding it with distractors 12 of progressively increasing heights. The distractor 12 is then left in the disc space and the centering location may be checked by placing the c-arm back into the AP position. If the location is confirmed as correct (e.g., centered), the c-arm is turned back into the lateral position. The spinal implant 1 is filled with autologous bone graft or bone graft substitute. The distractor 12 is removed and the spinal implant 1 is inserted under c-arm fluoroscopy visualization. The process according to the present invention does not use a secondary distractor; rather, distraction of the disc space is provided by the spinal implant 1 itself (i.e., the implant 1 itself is used as a distractor).

Certain embodiments of the present invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1 (a 32 or 36 mm window in the annulus is typically suitable for insertion). The process according to the present invention minimizes, if it does not eliminate, the cutting of bone. The endplates are cleaned of all cartilage with a curette, however, and a size-specific rasp (or broach) may then be used.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the present surgical method minimize endplate bone removal on the whole, while still allowing for some removal along the vertebral endplate far lateral edges where the subchondral bone is thickest. Still further, certain embodiments of the present interbody spinal implant 1 include smooth, rounded, and highly radiused posterior portions and lateral sides which may minimize extraneous bone removal for endplate preparation and reduce localized stress concentrations. Thus, interbody surgical implants 1 and methods of using them, as now taught, are particularly useful in preserving the natural arch of the vertebral endplate and minimizing the chance of implant subsidence.

Because the endplates are spared during the process of inserting the spinal implant 1, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Interbody spinal implants 1 of the present invention are durable and can be impacted between the endplates with standard instrumentation. Therefore, certain embodiments of the present invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, those embodiments having a surface roughened topography 80, as now taught, may lessen the risk of excessive bone removal during distraction as compared to implants having teeth, ridges, or threads currently known in the art even in view of a press-fit surgical distraction method. Nonetheless, once implanted, the interbody surgical implants 1, as now taught, may provide secure seating and prove difficult to remove. Thus, certain embodiments of the present interbody spinal implant 1 may maintain a position between the vertebral endplates due, at least in part, to resultant annular tension attributable to press-fit surgical implantation and, post-operatively, improved osteointegration at the top surface 10, the bottom surface 20, or both top and bottom surfaces.

As previously mentioned, surgical implants and methods, as now taught, tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implants 1, according to certain embodiments of the present invention, are particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implants 1 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implants 1, as now taught, may be used as the final distractor and thus maintain the relative position of the vertebrae without the need for secondary instrumentation.

The implant 1 according to certain embodiments of the present invention has a surface with the roughened topography 80. The roughened topography 80 includes features in repeating patterns that can be used to resist biologic-induced motion after placement in a joint space in contact with bone structures. The surface features are generated through a subtractive process and are further refined to remove sharp edges that could abrade the ambient bone while still providing sufficient friction to resist expulsion or movement. Macro features of the roughened topography 80 can be aligned to allow for insertion in opposition to a surface and to resist reverse motion from frictional contact with this surface. Repeating patterns, depth of features, spacing of various shaped features, and arraignment and overlapping of them in respect to others of a similar size and shape can also be used to develop designed composite patterns. As healing advances, the micro and nano surface modifications work in concert with the ambient biological actions occurring during the healing and fusion process. Biological structures will be stimulated especially at the nano feature level to produce biologic products that cause hard tissue formation with connections to the implant structure.

The implant 1 improves joint fusion through a balanced combination of structural features (a) designed and manufactured using a specific process, and (b) implanted using a surgical technique and method that results in initial mechanical fixation, allows for rapid bone growth during the healing process, and stimulates bone growth and fusion while reducing surgical treatment times. Some of implant surfaces have macro, micro and nano features; others have only micro and nano features. Regardless, the combinations of feature shapes aid in implantation and bone growth stimulation.

The shapes of the features are combined in a balanced manner with a conservative surgical procedure to improve recovery and fusion rates and reduce surgical operatory time. Implants that are placed within joint spaces following the practice of preserving structural bone, for example preserving the vertebral endplates in intervertebral procedures, through a defined and conservative surgical technique using specifically designed instrumentation can enhance fusion of the joint space. Therefore, the present invention encompasses a method for implanting the interbody implant 1 using a surgical procedure that preserves the bone structure of the vertebral endplates during preparation of the implant socket using instruments having bone-preserving features and surfaces. The method preserves the bone structures which the implant 1 contacts throughout the healing process, but retains a level of friction between the implant 1 and the bones of the vertebrae contributing to the fusion and healing process.

Existing implantation practices did not preserve critical structures, especially the vertebral endplates, during the surgical procedures. In addition, some of the existing implant devices are not designed with features that preserve critical bone structures during or after implantation. The structures and features of the implant 1 and the system of instruments used in connection with the implant 1, in accordance with the present invention, are designed to work in concert to preserve the endplate bone structures of the vertebral body. The surface preparation of the implant 1 provides for friction generation within the disc space but is not too aggressive which preserves the bone structures with which it is in contact.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. A process for fabricating bioactive vertebral endplate bone-contacting surfaces on a spinal implant, comprising:
   providing a spinal implant comprising titanium or an alloy of titanium, aluminum, and vanadium having one or more vertebral endplate bone-contacting surfaces;
   acid-etching or machining the one or more vertebral endplate bone-contacting surfaces to form macro-scale structural features;
   following the acid etching or machining step, abrasive media blasting the one or more vertebral endplate bone-contacting surfaces to form micro-scale structural features that overlap the macro-scale structural features; and
   following the abrasive media blasting step, mildly acid-etching the one or more vertebral endplate bone-contacting surfaces to form nano-scale structural features that overlap the macro-scale structural features and the micro-scale structural features,
   thereby forming the final and completed bioactive vertebral endplate bone-contacting surfaces on the spinal implant, provided that the process does not include at any time applying a coating to any of the vertebral endplate bone-contacting surfaces and does not include at any time embedding surface contaminants into any of the vertebral endplate bone-contacting surfaces.

2. The process according to claim 1, wherein the abrasive media blasting comprises blasting the one or more vertebral endplate bone-contacting surfaces with media comprising aluminum oxide particles.

3. The process according to claim 1, wherein the spinal implant is configured for use in a lumbar fusion procedure.

4. The process according to claim 1, wherein the spinal implant is configured for use in a cervical fusion procedure.

5. The process according to claim 1, wherein the macro-scale structural features are roughly spherical in shape.

6. The process according to claim 5, wherein the macro-scale structural features lack undercuts or protruding sharp edges.

7. The process according to claim 1, wherein the macro-scale features, the micro-scale features, and the nano-scale features are oriented in opposition to the insertion direction of the implant.

8. The process according to claim 1, wherein the one or more bioactive vertebral endplate bone-contacting surfaces are irregular.

9. The process according to claim 1, wherein the step of acid-etching or machining comprises acid-etching or machining a first-cut to produce macro-scale features having the smallest diameter and greatest depth, then acid-etching or machining a second cut to produce macro-scale features having an intermediate diameter and depth, and then acid-etching or machining a third cut to produce macro-scale features having the greatest diameter and smallest depth.

10. The process according to claim 1, wherein the macro-scale structural features have an amplitude of from about 20 to about 200 microns, a peak-to-valley height of from about 40 to about 500 microns, and a mean spacing of from about 400 to about 2000 microns.

11. The process according to claim 1, wherein the micro-scale structural features have an amplitude of from about 1 to about 20 microns, a peak-to-valley height of from about 2 to about 40 microns, and a mean spacing of from about 20 to about 400 microns.

12. The process according to claim 1, wherein the nano-scale structural features have an amplitude of from about 0.010 to about 1 microns, a peak-to-valley height of from about 0.2 to about 2 microns, and a mean spacing of from about 0.5 to about 20 microns.

13. The process according to claim 1, wherein the step of mildly acid etching comprises etching the one or more vertebral endplate bone-contacting surfaces with aqueous hydrochloric acid to form the nano-scale structural features.

14. A process for fabricating bioactive vertebral endplate bone-contacting surfaces on a spinal implant, comprising:

providing a spinal implant comprising titanium or an alloy of titanium, aluminum, and vanadium having one or more vertebral endplate bone-contacting surfaces;

acid-etching or machining the one or more vertebral endplate bone-contacting surfaces to form macro-scale structural features;

following the acid etching or machining step, abrasive media blasting the one or more vertebral endplate bone-contacting surfaces to form micro-scale structural features that overlap the macro-scale structural features, such overlap avoiding undercuts or protruding sharp edges; and following the abrasive media blasting step, mildly acid-etching the one or more vertebral endplate bone-contacting surfaces to form nano-scale structural features that overlap the macro-scale structural features and the micro-scale structural features, such overlap avoiding undercuts or protruding sharp edges, thereby forming the final and completed bioactive vertebral endplate bone-contacting surfaces on the spinal implant, provided that the process does not include at any time applying a coating to any of the vertebral endplate bone-contacting surfaces and does not include at any time embedding surface contaminants into any of the vertebral endplate bone-contacting surfaces.

15. The process according to claim 14, wherein the macro-scale structural features are roughly spherical in shape.

16. The process according to claim 15, wherein the macro-scale structural features lack undercuts or protruding sharp edges.

17. The process according to claim 14, wherein the macro-scale features, the micro-scale features, and the nano-scale features are oriented in opposition to the insertion direction of the implant.

18. The process according to claim 14, wherein the one or more bioactive vertebral endplate bone-contacting surfaces are irregular.

19. The process according to claim 14, wherein the step of acid-etching or machining comprises add-etching or machining a first-cut to produce macro-scale features having the smallest diameter and greatest depth, then acid-etching or machining a second cut to produce macro-scale features having an intermediate diameter and depth, and then acid-etching or machining a third cut to produce macro-scale features having the greatest diameter and smallest depth.

20. A process for fabricating bioactive vertebral endplate bone-contacting surfaces on a spinal implant, comprising:

providing a spinal implant comprising titanium or an alloy of titanium, aluminum, and vanadium having one or more vertebral endplate bone-contacting surfaces;

acid-etching or machining the one or more vertebral endplate bone-contacting surfaces to form macro-scale structural features that are roughly spherical in shape and lack undercuts or protruding sharp edges;

following the acid etching or machining step, abrasive media blasting the one or more vertebral endplate bone-contacting surfaces to form micro-scale structural features that overlap the macro-scale structural features; and following the abrasive media blasting step, mildly acid-etching the one or more vertebral endplate bone-contacting surfaces to form nano-scale structural features that overlap the macro-scale structural features and the micro-scale structural features, thereby forming the final and completed bioactive vertebral endplate bone-contacting surfaces on the spinal implant, provided that the process does not include at any time applying a coating to any of the vertebral endplate bone-contacting surfaces and does not include at any time embedding surface contaminants into any of the vertebral endplate bone-contacting surfaces, wherein the macro-scale features, the micro-scale features, and the nano-scale features are oriented in opposition to the insertion direction of the implant.

* * * * *